United States Patent [19]
Lee et al.

[11] Patent Number: 5,859,042
[45] Date of Patent: Jan. 12, 1999

[54] FIVE MEMBERED HETEROCYCLIC COMPOUNDS

[75] Inventors: Sung Jai Lee, Montville, N.J.; Takuya Seko, Osaka, Japan; Manton Rodgers Frierson, Bay City, Mich.; Jagadish Chandra Sircar, San Diego, Calif.; Charles Xian Cao, Branchburg, N.J.

[73] Assignee: Ono Pharmaceutical Co., Ltd., Osaka, Japan

[21] Appl. No.: 793,983

[22] PCT Filed: Sep. 27, 1995

[86] PCT No.: PCT/US95/11962

§ 371 Date: Mar. 13, 1997

§ 102(e) Date: Mar. 13, 1997

[87] PCT Pub. No.: WO96/10013

PCT Pub. Date: Apr. 4, 1996

[51] Int. Cl.$^6$ .................... A61K 31/415; A61K 31/40; C07D 233/58; C07D 207/323

[52] U.S. Cl. .................... 514/400; 514/414; 514/422; 514/423; 514/448; 548/341.5; 548/465; 548/518; 548/525; 548/527; 548/539; 548/540; 549/70

[58] Field of Search ................ 548/341.5, 518, 548/525, 527, 539, 540, 465; 514/400, 422, 423, 414, 448; 549/70

[56] References Cited

U.S. PATENT DOCUMENTS

| | | | |
|---|---|---|---|
| 3,801,605 | 4/1974 | Carson | 260/347.3 |
| 3,865,840 | 2/1975 | Carson | 260/326.46 |
| 3,952,012 | 4/1976 | Carson | 260/326.47 |
| 4,187,230 | 2/1980 | Wiegand et al. | 260/326.47 |

FOREIGN PATENT DOCUMENTS

| | | |
|---|---|---|
| 0300688 | 1/1989 | European Pat. Off. . |
| 1574570 | 7/1969 | France . |
| 4325204 | 2/1995 | Germany . |
| 1195628 | 7/1968 | United Kingdom . |
| 1327308 | 8/1973 | United Kingdom . |
| 1331505 | 9/1973 | United Kingdom . |
| 1390866 | 4/1975 | United Kingdom . |
| 9313099 | 7/1993 | WIPO . |

OTHER PUBLICATIONS

CA 121: 230625d Synthesis of 5–(p–toluoyl)–1–methylpyrrole–2–acetic acid [Tolmetin], p. 1076, Choi et al, 1994.
CA 109: 210828w Antibacterial and antifungal compounds, . . . trioostaton A, p. 643, Corelli et al, 1968.
CA 107: 7131x Synthietic studies of tolmetin analogs, p. 647, Hayashi et al, 1987.
CA 94: 192131d 1–Methyl–. . . p–toluoylpyrroles, p. 641, 1981.
CA 93: 31846e Purity determination . . . chromatography, p. 335, Ko et al, 1980.
CA 92: 146526x Carbenoid chemistry.Reaction . . . diazoacetate, p. 567, Olofson et al, 1980.
CA121:291906 Covalent . . . significance, Benet et al., 1994.
CA121:292263 Effects of . . . neutrophil, Kim et al, 1994.
Farmaco Ed. Sc. vol. 41, No. 4, Issued 1986, S. Massa, et al. "Agenti Antiinfiammatori Non–Steroidei", pp. 281–291.

*Primary Examiner*—Joseph K. McKane
*Attorney, Agent, or Firm*—Stevens, Davis, Miller & Mosher, L.L.P.

[57] ABSTRACT

The instant invention is related to 5-membered heterocyclic compounds and pharmaceutical compositions which possess inhibitory activity on 5 alpha-reductase.

24 Claims, No Drawings

FIVE MEMBERED HETEROCYCLIC COMPOUNDS

This application is a 371 of PCT/US95/1962 filed Sep. 27, 1995.

SUMMARY

This invention is related to five membered heterocyclic compounds. More particularly, this invention is related to:
(1) An inhibitory agent on 5α-reductase which comprises a five membered heterocyclic compound of the formula (Ia):

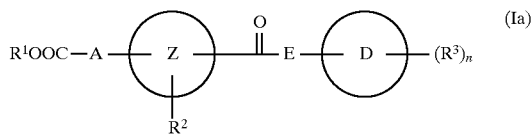

wherein all the symbols are the same meaning as hereafter defined, and non-toxic salts thereof as active ingredient,
(2) a five membered heterocyclic compound of the formula (Ib):

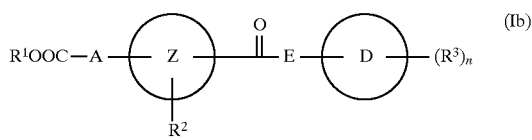

wherein all the symbols are the same meaning as hereafter defined, and non-toxic salts thereof,
(3) process for the preparation of a five membered heterocyclic ring compound of the formula (Ib) and non-toxic salts thereof.

BACKGROUND

So far as the origin of androgenic alopecia, many theories are exposited such as (1) imbalance of hormones, (2) genetics, (3) circulatory failure, (4) nutrition. And it has been suggested that testosterone (androgenic hormone) played an important role on the generation of hairs. The relation between testosterone and androgenic alopecia is as follows:
(i) first, testosterone biosynthesized in testis is converted into dihydrotestosterone(DHT) by 5α-reductase existed in hair follicle, sebaceous gland etc. at the head,
(ii) DHT reduces the activities of adenyl cyclase remarkably,
(iii) it induces fall of the level of cyclic-AMP in cells,
(iv) last, it induces lowering of energy generation of hairs and the limbus and suppressing of protein synthesis [Biochem. Biophys. Res. Commun., 41,884(1970)].

Large quantities of metabolites by 5α-reductase such as DHT etc. in hair follicles of androgenic alopecia-patient exist more than that in females or healthy males. [J. Clin. Endocr., 38, 811(1974)].

It was reported that DHT converted from testosterone by 5α-reductase also plays an important physiological role in the generation of acnes (acne, pimple etc.) other than androgenic alopecia [Br. J. Dermatol., 91, 123(1974); J. Invest. Dermatol., 56, 366(1971)].

It has been clear that DHT also plays an important role in the generation and the development of prostatic hypertrophy [J. Steroid Biochemistry, 11, 609(1979); J. Clinical Endocrinol and Metabolism, 56, 139(1983)].

And, it is thought that DHT is also related to prostatic cancer.

Recently, it was confirmed that the existence of at least two 5α-reductase isozymes (I type and II type) in human. There are differences between these isozymes about gene formation, of course, biochemical properties, expression styles, hereditary properties and pharmacological properties. [Nature, 354, 159–161(1991); J. Clin, Invest., 89,293–300 (1992)]. Among two type isozymes, it is considered that II type one exists more than I type one in human testis.

Therefore, it was confirmed that inhibition of a change from testosterone to DHT by 5α-reductase inhibitor is useful for above diseases.

Now, research and development of 5α-reductase inhibitors are carried out energetically. Many kinds of compounds are synthesized and tested. 5α-Reductase inhibitors are largely divided into compounds having steroidal structure and compounds having non-steroidal structure.

A representation of steroidal compound is finasteride, shown by below formula, and the compound is available in the market.

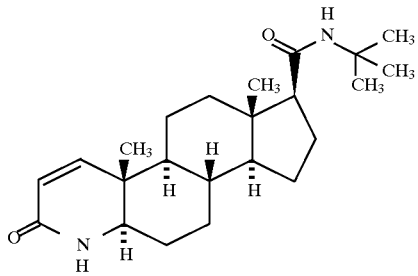

As a non-steroidal compound, ONO-3805 shown below formula is known.

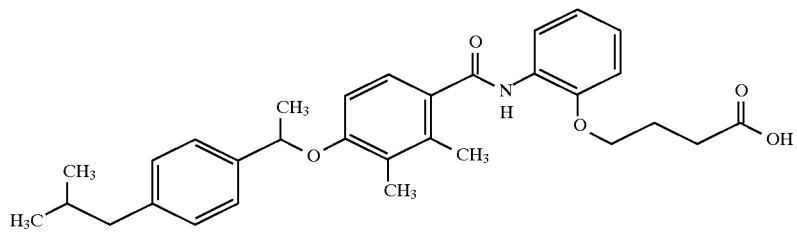

RELATED ARTS

Non-steroidal compounds possessing 5α-reductase inhibitory activity, for example, are the following:

(1) In the specification of WO9324442, benzoic acid derivatives are disclosed.

(2) In the specification of European Patent Publication Number 458207, WO9303012, WO 9305019 and WO9316996, indole derivatives are disclosed.

(3) In the specification of European Patent Publication Number 519353, indolizine derivatives are disclosed.

(4) In the specification of WO9313099, the compound of the formula (A) is disclosed.

wherein $R^{1A}$ is carboxy (lower) alkyl or protected carboxy (lower)alkyl, $R^{2A}$ is optionally substituted aralkyl, $X^A$ is optionally substituted arylene, $Y^A$ is —O— or —$NR^{6A}$—, in which $R^{6A}$ is hydrogen, lower alkyl, optionally substituted aralkyl or amino-protective group, and $A^A$ is a bivalent radical derived from imidazopyridine, azulene, thiophene, pyrrolo[2,3-b]pyridine, quinolone, indazole or dihydrobenzimidazole, each of which may be substituted by one or more suitable substituent(s).

(5) On the 24th National Medicinal Chemistry Symposium (Jun. 21–24, 1994), it was discussed that benzoic acid derivatives and indole derivatives having 5α-reductase inhibitory activity.

Meanwhile, (6) in the specification of GB1195628, the compound of the formula (B):

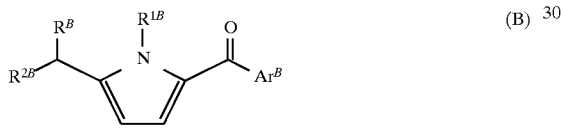

wherein $Ar^B$ is phenyl, phenyl substituted by one or more halogen, lower alkyl, lower alkoxy, $NO_2$, $NH_2$, CN or $SCH_3$; $R^B$ is hydrogen, lower alkyl; $R^{1B}$ is hydrogen, lower alkyl, benzyl; $R^{2B}$ is CN, COOH, COO(lower alkyl), CONH2, CONH(lower alkyl), CON(lower alkyl)$_2$, is disclosed to be useful as antiinflammatory. For example, the compound of the formula:

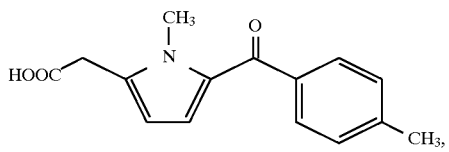

which is available in the market as an antiinflammatory agent (Tolmetin), is disclosed.

(7) In the specification of GB1327308, the compound of the formula (C):

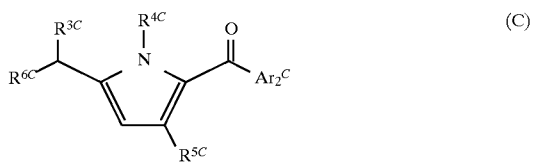

wherein $Ar_2^C$ is thienyl, 5-methylthienyl or substituted phenyl; $R^{3C}$ is COOH, COO(lower alkyl) etc.; $R^{4C}$ is lower alkyl; $R^{5C}$ is lower alkyl; $R^{6C}$ is hydrogen, lower alkyl, is disclosed to be useful as antiinflammatory. For example, the compound of the formula:

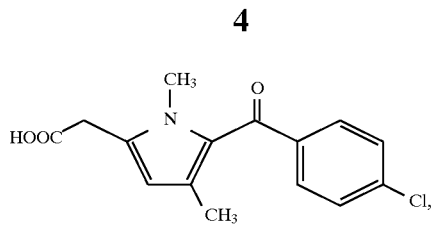

which is available in the market as an analgesic, antiinflammatory agent (Zomepirac), is disclosed.

(8) In the specification of GB 1331505, the compound of the formula (D):

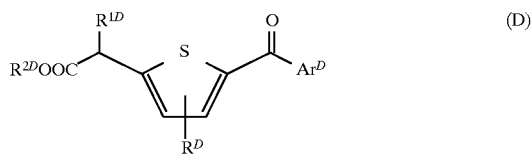

wherein $R^D$ is hydrogen, C1–4 alkyl; $R^{1D}$ is hydrogen, C1–4 alkyl; R2D is hydrogen, lower alkyl etc.; $Ar^D$ is phenyl, cyclohexyl, heterocyclic group, is disclosed to be useful as antiinflammatory.

(9) In the specification of U.S. Pat. No. 3,801,605, the compound of the formula (E):

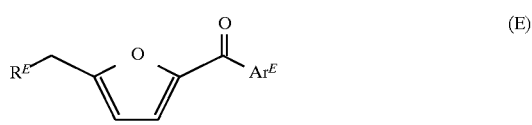

wherein $R^E$ is COOH, (C1–5 alkoxy)carbonyl, CN, $CONH_2$; $Ar^E$ is phenyl, phenyl substituted by halogen, $SCH_3$, C1–5 alkyl or alkoxy, is disclosed to be useful as antiphlogistics.

(10) In the specification of GB1390866, the compound of the formula (F):

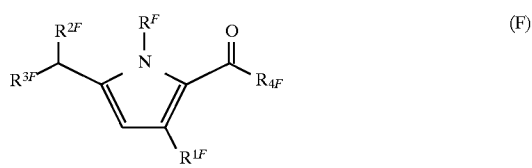

wherein $R^F$ is hydrogen, lower alkyl; $R^{1F}$ is hydrogen, methyl; $R^{2F}$ is hydrogen, methyl; $r^{3f}$ is —COOH, —COO (lower alkyl); $R^{4F}$ is benzyl, cyclopentyl, cyclohexyl, is disclosed to be useful as antiinflammatory. For example, the compounds of the formulae:

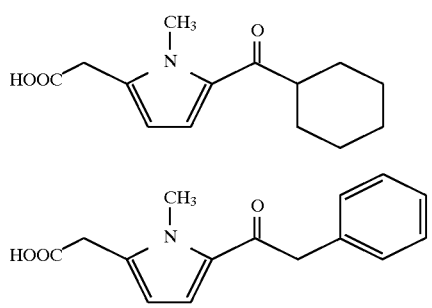

and ethyl ester thereof are disclosed.

(11) The compounds of the formulae:

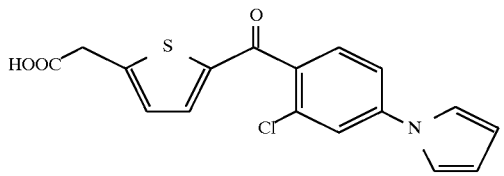

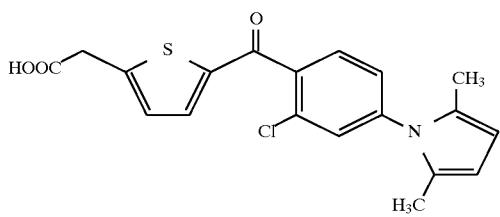

and methyl ester thereof are disclosed to be useful as antiinflammatory (Farmaco Ed. Sc., 41(4), 281–289 (1986)).

(12) In the specification of DE4325204, published on Feb. 2, 1995, the compound of the formula (G-I), (G-II), (G-III), (G-IV):

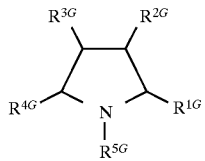 (G-I)

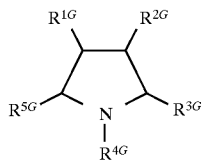 (G-II)

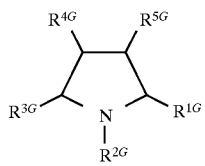 (G-III)

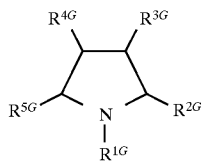 (G-IV)

wherein $R^{1G}$ is —COOH or $X^G$—COOH in which $X^G$ is C1–8alkyl, C2–8 alkenyl or alkynyl etc.; $R^{3G}$ is —CO—CH$_3$, —CO—$Y^G$ or —COY$^G$-Aryl in which $Y^G$ is C2–19 alkyl, alkenyl or alkynyl etc., $R^{2G}$, $R^{4G}$, $R^{5G}$ is hydrogen, C1–20 alkyl, C2–20 alkenyl or alkynyl, Aryl, —$Z^G$-Aryl etc., in which $Z^G$ is C1–20 alkyl, C2–10 alkenyl or alkynyl etc; is disclosed to be useful as phospholipase A2 inhibitors.

(13) In the specification of JP Kokai Hei 7-138227 published on May 30, 1995, the compounds of the formula (H):

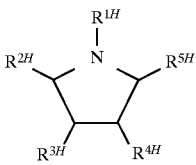 (H)

wherein $R^{1H}$ is (i) hydrogen, (ii) C1–3 saturated or unsaturated alkyl optionally substituted by OH, SH, halogen, COOH, alkoxy, alkoxycarbonyl or aryloxycarbonyl, (iii) COOH, alkoxycarbonyl, aryloxycarbonyl, (iv) benzoyl optionally substituted by halogen, (v) phenyl or tosyl, (vi) carbonyl group connected with alkoxycarbonylethyl; $R^{2H}$ and $R^{5H}$ is (i) hydrogen, (ii) methyl optionally substituted by OH, COOH, alkoxycarbonyl, (iii) —CHO, COOH, acethyl, propionyl, (iv) benzoyl optionally substituted by halogen (v) carbonyl group connected with alkoxycarbonylethyl, (vi) 3-alkoxycarbonyl-2-alkoxy-2-propenyl, (vii) nitrophenyl;

$R^{3H}$ and $R^{4H}$ is (i) hydrogen, (ii) aryloxycarbonyl, (iii) carbonyl group connected with methyl or ethyl substituted by alkoxycarbonyl, (iv) benzoyl optionally substituted by halogen, is disclosed to be useful as growth of hair.

PURPOSE OF INVENTION

Energetic investigation have been carried out in order to discover compounds of non-steroidal formula having 5α-reductase inhibitory activity, the present inventors have found that compounds of the formula (Ia) having 5α-reductase inhibitory activity and have accomplished the present invention.

COMPARISON WITH THE RELATED ARTS

The compounds disclosed in the related arts (1), (2), (3) and (5) are benzoic acid derivatives, indole derivatives or indolizine derivatives. The compounds of the formula (Ia) of the present invention are pyrrole, thiophene, furan, imidazole, thiazole, oxazole and triazole derivatives. Therefore, the compounds of the present invention differ from those compounds.

In case of $X^A$ is phenylene or naphthalene and $A^A$ is thiophene, the compound of the formula (A) in the specification of WO9313099 of the related arts (4) is the compound of the following formula (Aa):

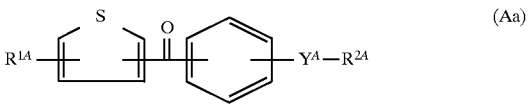 (Aa)

wherein the all symbols are the same meaning as hereinbefore defined.

The compounds which $\textcircled{Z}$ is thiophene in the formula (Ia) of the present invention are following thiophene compounds.

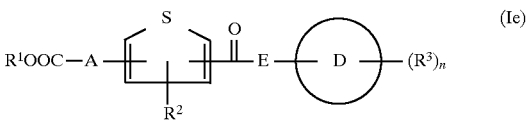 (Ie)

However, those compounds of the formula (Ie) in the present invention are not overlapped with the above compounds of the formula (Aa). In the specification of WO9313099, the following two thiophene compounds are described.

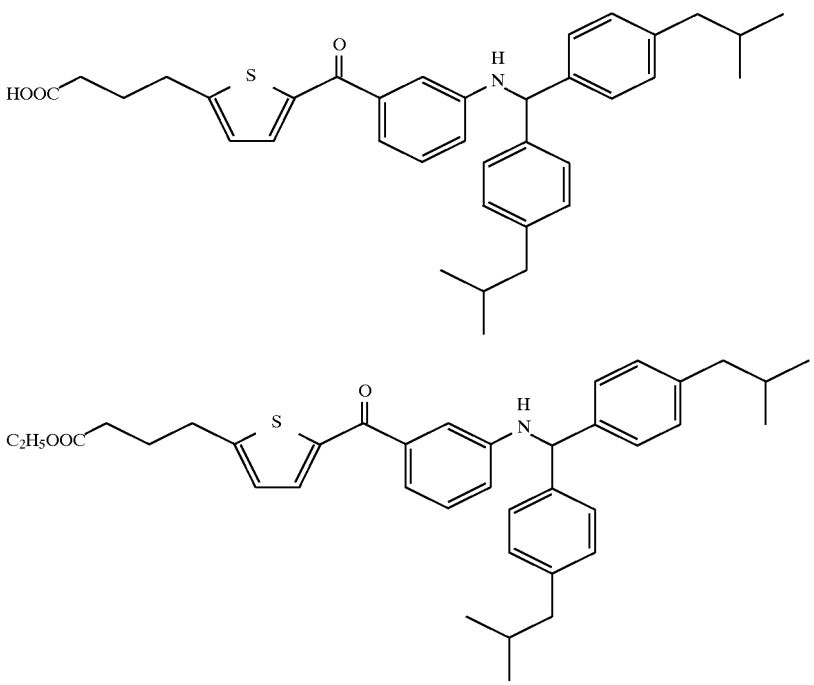

The compounds in the related arts (6), (7), (8), (9), (10) and (11) are disclosed to be useful as antiinflammatory. There are not description that the compound in the related arts (6), (7), (8), (9), (10) and (11) possess 5α-reductase inhibitory activity. It is not able to expect at all that the compounds having pyrrole ring, thiophene ring or furan ring possess 5α-reductase inhibitory activity.

The compounds wherein $(Z)$ is pyrrole included nitrogen substituted by $R^4$; E is C1–6 alkylene; $(D)$ is benzene; $R^1$ is hydrogen; $R^3$ is $R^{3-1}$; $R^{3-1}$ is hydrogen, C1–6 alkyl, C1–6 alkoxy, halogen, nitro, methylthio, trifluoromethyl; the other symbols are the same meaning as hereinbefore defined; in the formula (Ia) of the present invention represents the following compounds of the formula (If).

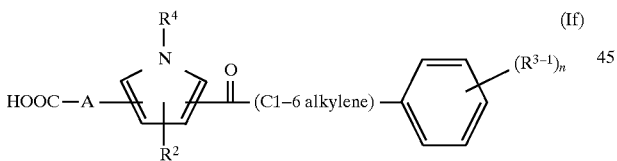

These compounds of the formula (If) are broadly overlapped with the compounds wherein $R^{3G}$ is —CO—$Y^G$-Aryl in the formula (G-I), (G-II) and (G-III) in the specification of DE-4325204 of the related art (12). However, in the specification of DE 4325204, the only one example compound wherein $R^{3G}$ is —CO—$Y^G$-Aryl is disclosed, but is not included in the extent of the present invention. Moreover, the compounds in the specification of DE4325204 are disclosed to be useful as phospholipase A2 inhibitors. There is no description that the compounds in the specification of DE4325204 possess 5α-reductase inhibitory activity. The compounds of the present invention are not overlapped with the compound of JP Kokai Hei 7-138227 of the related art (13).

DISCLOSURE OF THE INVENTION

The present invention is related to novel use of known compounds, novel compounds, use of the novel compounds and process for the preparation of the novel compounds.

Accordingly, the present invention is related to 1) An inhibitory agent on 5α-reductase which comprises a compound of the formula (Ia):

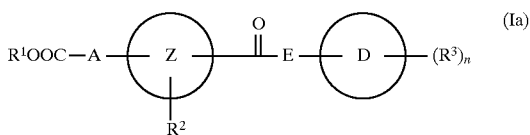

wherein $(Z)$ is pyrrole included nitrogen substituted by $R^4$, thiophene, furan, imidazole included nitrogen substituted by $R^4$, thiazole, oxazole, triazole included nitrogen substituted by $R^4$, in which $R^4$ is hydrogen, C1–4 alkyl, phenyl or phenyl(C1–4)alkyl;

A is bond, C1–6 alkylene or C2–6 alkenylene;

E is bond or C1–6 alkylene;

$(D)$ is benzene, C4–7 cycloalkane, naphthalene, benzo(C4–7)cycloalkane, indene, cyclopenta(C4–7)cycloalkane,

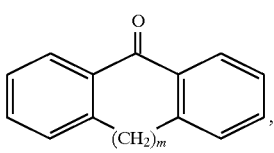

in which m is 0 or 1, or benzene fused 4–7 membered heterocyclic ring containing one nitrogen, one sulfur or one oxygen atom;

$R^1$ is hydrogen or C1–4 alkyl;

$R^2$ is hydrogen or C1–4 alkyl;

n is 1–3;

$R^3$ each, independently, is (1) hydrogen, C1–6 alkyl, C1–6 alkoxy, halogen, nitro, methylthio, trifluoromethyl or cyano, (2) —Q—T—U—$R^5$ in which Q is bond or C1–6 alkylene;

T is bond, —O—,

—S—, —SO$_2$—, —NR$^7$— or —NR$^7$CO—, in which R$^7$ is hydrogen, C1–4 alkyl, phenyl or phenyl(C1–4)alkyl and nitrogen atom in —NR$^7$CO— may be connected with —Q— or —U—;

U is bond, C1–6 alkylene, C2–6 alkenylene, C2–6 alkynylene or C1–6 alkylene —O—, in which oxygen atom can be connected with R$^5$ only;

R$^5$ is (i) C4–7 cycloalkyl, (ii) phenyl, (iii) diphenylmethyl or (iv) 4–7 membered heterocyclic ring containing one nitrogen, one sulfur or one oxygen, or the benzene fused 4–7 membered heterocyclic ring containing one nitrogen, one sulfur or one oxygen, or rings in (i), (ii), (iii), (iv) of R$^5$ may be substituted by 1–3 of C1–10 alkyl, C1–10 alkoxy, hydroxy, halogen, trifluoromethyl, nitro or COR$^6$, in which R$^6$ is C1–4 alkyl, NR$^8$R$^9$, in which R$^8$ and R$^9$ each, independently, is hydrogen or C1–4 alkyl; or —Q—T—U—R$^5$ is C7–10 alkyl, C7–10 alkoxy;

or non-toxic salts thereof, with the proviso that, the compounds wherein (i) T is —O—, or —NR$^7$—, and U is bond and R$^5$ is diphenylmethyl in —Q—T—U—R$^5$ represented by R$^3$, when Ⓩ is thiophene, E is bond and Ⓓ is benzene or napthalene, (ii) T is —O—, or —NR$^7$—, and U is C1–6 alkylene and R$^5$ is phenyl or diphenylmethyl in —Q—T—U—R$^5$ represented by R$^3$, when Ⓩ is thiophene, E is bond and Ⓓ is benzene or naphthalene, (iii) Ⓩ is pyrrole included nitrogen substituted by R$^4$, in which R$^4$ is hydrogen, C1–3 alkyl or phenyl, A is bond or methylene, E is bond, Ⓓ is benzene, R$^2$ is hydrogen or methyl and R$^3$ each, independently, is hydrogen or halogen, are excluded, 2) a compound of the formula (Ib):

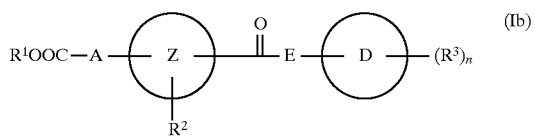

wherein Ⓩ is pyrrole included nitrogen substituted by R$^4$, thiophene, furan, imidazole included nitrogen substituted by R$^4$, thiazole, oxazole, triazole included nitrogen substituted by R$^4$, in which R$^4$ is hydrogen, C1–4 alkyl, phenyl or phenyl(C1–4)alkyl;

A is bond, C1–6 alkylene or C2–6 alkenylene;

E is bond or C1–6 alkylene;

Ⓓ is benzene, C4–7 cycloalkane, naphthalene, benzo (C4–7)cycloalkane, indene, cyclopenta(C4–7) cycloalkane,

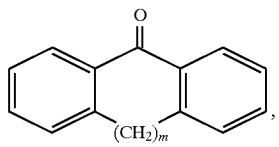

in which m is 0 or 1, or benzene fused 4–7 membered heterocyclic ring containing one nitrogen, one sulfur or one oxygen atom;

R$^1$ is hydrogen or C1–4 alkyl;

R$^2$ is hydrogen or C1–4 alkyl;

n is 1–3;

R$^3$ each, independently, is (1) hydrogen, C1–6 alkyl, C1–6 alkoxy, halogen, nitro, methylthio, trifluoromethyl or cyano, (2) —Q—T—U—R$^5$ in which Q is bond or C1–6 alkylene;

T is bond, —O—,

—S—, —SO$_2$—, —NR$^7$— or —NR$^7$CO—, in which R$^7$ is hydrogen, C1–4 alkyl, phenyl or phenyl(C1–4)alkyl and nitrogen atom in —NR$^7$CO— may be connected with —Q— or —U—;

U is bond, C1–6 alkylene, C2–6 alkenylene, C2–6 alkynylene or C1–6 alkylene —O—, in which oxygen atom can be connected with R$^5$ only;

R$^5$ is (i) C4–7 cycloalkyl, (ii) phenyl, (iii) diphenylmethyl or (iv) 4–7 membered heterocyclic ring containing one nitrogen, one sulfur or one oxygen, or the benzene fused 4–7 membered heterocyclic ring containing one nitrogen, one sulfur or one oxygen, or rings in (i), (ii), (iii), (iv) of R$^5$ may be substituted by 1–3 of C1–10 alkyl, C1–10 alkoxy, hydroxy, halogen, trifluoromethyl, nitro or COR$^6$, in which R$^6$ is C1–4 alkyl, NR$^8$R$^9$, in which R$^8$ and R$^9$ each, independently, is hydrogen or C1–4 alkyl;

or —Q—T—U—R$^5$ is C7–10 alkyl, C7–10 alkoxy; or non-toxic salts thereof, with the proviso that, (a) compounds wherein (i) T is —O—, or —NR$^7$—, and U is bond and R$^5$ is diphenylmethyl in —Q—T—U—R$^5$ represented by R$^3$, when Ⓩ is thiophene, E is bond and Ⓓ is benzene or naphthalene, (ii) T is —O—, or —NR$^7$—, and U is C1–6 alkylene and R$^5$ is phenyl or diphenylmethyl in —Q—T—U—R$^5$ represented by R$^3$, when Ⓩ is thiophene, E is bond and Ⓓ is benzene or napthalene, are excluded;

(b) at least one R$^3$ of (R$^3$)$_n$ is a substituent selected from group (2) that is —Q—T—U—R$^5$, when E is bond and Ⓓ is benzene;

(c) all R$^3$ of (R$^3$)$_n$ are not hydrogen at the same time, when E is bond and Ⓓ is C4–7 cycloalkane, or E is methylene and Ⓓ is benzene;

(d) 2-[5-[2-chloro-4-(1H-pyrrol-1-yl)benzoyl]thiophen-2-yl]acetic acid and methyl ester thereof and 2-[5-[2-chloro-4-(2,5-dimethyl-1H-pyrrol-1-yl)benzoyl] thiophen-2-yl]acetic methyl ester thereof are excluded.

3) process for the preparation of a compound of the formula (Ib) and non-toxic salts thereof.

In the present invention, C4–7 cycloalkane of the following formula:

Ⓓ means cyclobutane, cyclopentane, cyclohexane, cycloheptane.

In the present invention, benzo(C4–7)cycloalkane of the following formula:

Ⓓ means benzocyclobutane, 2,3-dihydroindene, 1,2,3,4-tetrahydronaphthalene, 1,2,3,4,5-pentahydrobenzocycloheptene.

In the present invention, cyclopenta(C4–7)cycloalkane of the following formula:

Ⓓ means cyclopentacyclobutane, cyclopentacyclopentane, cyclopentacyclohexane, cyclopentacycloheptane.

In the present invention,

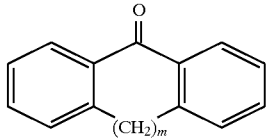

of the following formula:

Ⓓ means

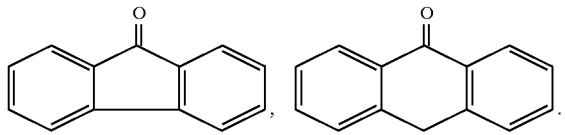

In the present invention, C1–6 alkylene represented by A, E, Q or U and included in C1–6 alkylene —O— represented by U, means methylene, ethylene, trimethylene, tetramethylene, pentamethylene, hexamethylene and isomeric groups thereof.

C2–6 alkenylene represented by A or U mean vinylene, propenylene, butenylene, pentenylene, hexenylene and isomeric groups thereof.

C2–6 alkynylene represented by U means ethynylene, propynylene, butenylene, pentenylene, hexenylene and isomeric groups thereof.

C1–4 alkyl represented by $R^1$, $R^2$, $R^4$, $R^6$, $R^7$, $R^8$ or $R^9$ mean methyl, ethyl, propyl, butyl and isomeric groups thereof.

C1–6 alkyl represented by $R^3$ means methyl, ethyl, propyl, butyl, pentyl, hexyl and isomeric groups thereof.

C1–6 alkoxy represented by $R^3$ means methoxy, ethoxy, propoxy, butoxy, pentyloxy, hexyloxy and isomeric groups thereof.

Halogen represented by $R^3$ means fluorine, chlorine, bromine and iodine.

Phenyl(C1–4)alkyl represented by $R^4$ or $R^7$ means methyl, ethyl, propyl, butyl and isomeric groups thereof substituted by 1 of phenyl.

C4–7 cycloalkyl represented by $R^5$ means cyclobutyl, cyclopentyl, cyclohexyl and cycloheptyl.

4–7 membered heterocyclic ring containing one nitrogen represented by $R^5$ means, for example, pyrrole, pyridine, azepine and partially or fully saturated ring thereof.

Benzene fused 4–7 membered heterocyclic ring containing one nitrogen represented by $R^5$ or Ⓓ means, for example, indole, isoindole, quinoline, isoquinoline, benzoazepine and partially or fully saturated ring thereof (e.g. indoline, isoindoline).

4–7 membered heterocyclic ring containing one sulfur represented by $R^5$ means, for example, thiophene, thiain, thiepin and partially or fully saturated ring thereof.

Benzene fused 4–7 membered heterocyclic ring containing one sulfur represented by $R^5$ or Ⓓ means, for example, benzothiophene, benzothiain, benzothiepin and partially or fully saturated ring thereof.

4–7 membered heterocyclic ring containing one oxygen represented by $R^5$ means, for example, furan, pyran, oxepin and partially or fully saturated ring thereof.

Benzene fused 4–7 membered heterocyclic ring containing one oxygen represented by $R^5$ or Ⓓ means, for example, benzofuran, benzopyran, benzoxepine and partially or fully saturated ring thereof (e.g. chroman, isochroman).

C1–10 alkyl as substituents of rings in groups represented by $R^5$ means methyl, ethyl, propyl, butyl, pentyl, hexyl, heptyl, octyl, nonyl, decyl and isomeric groups thereof.

C1–10 alkoxy as substituents of rings in groups represented by $R^5$ means methoxy, ethoxy, propoxy, butoxy, pentyloxy, hexyloxy, heptyloxy, octyloxy, nonyloxy, decyloxy and isomeric groups thereof.

Halogen as substituents of rings in groups represented by $R^5$ means fluorine, chlorine, bromine and iodine.

C7–10 alkyl represented by —Q—T—U—$R^5$ means heptyl, octyl, nonyl, decyl and isomeric groups thereof.

C7–10 alkoxy represented by —Q—T—U—$R^5$ means heptyloxy, octyloxy, nonyloxy, decyloxy and isomeric groups thereof.

Preferable Compounds

In the compound of the present invention of the formula (Ia), the compounds of the following formula (Ia-A), (Ia-B), (Ia-C), (Ia-D), (Ia-E), (Ia-F), (Ia-G) and non-toxic salts thereof are preferable.

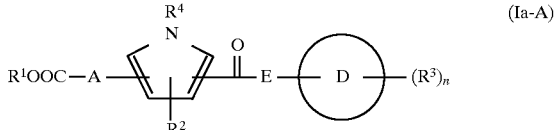

(Ia-A)

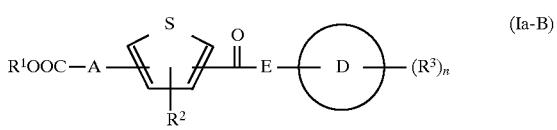

(Ia-B)

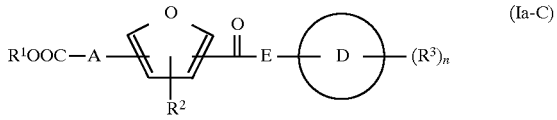

(Ia-C)

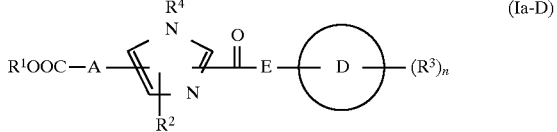

(Ia-D)

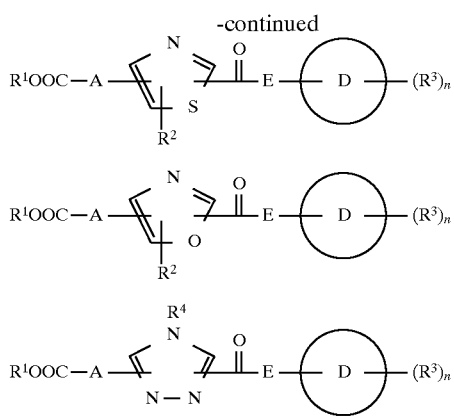 (Ia-E)

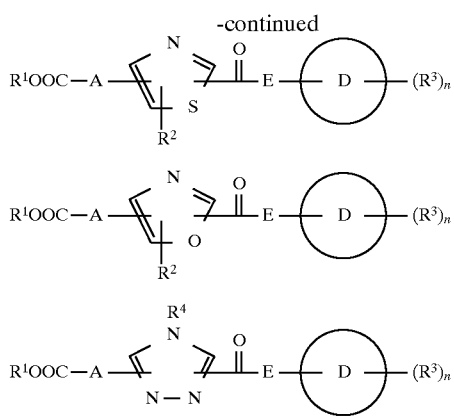 (Ia-F)

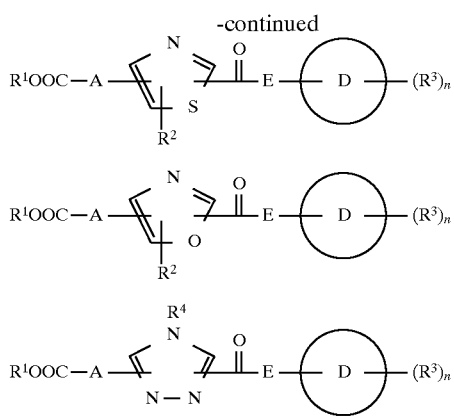 (Ia-G)

wherein all the symbols are the same meaning as hereinbefore defined.

And the compounds of the following formula (Ia-H), (Ia-I), (Ia-J) and non-toxic salts thereof are preferable.

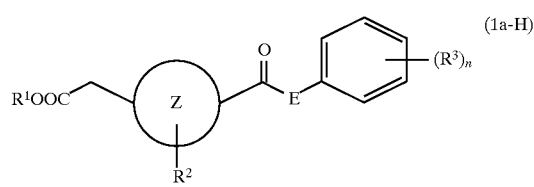 (1a-H)

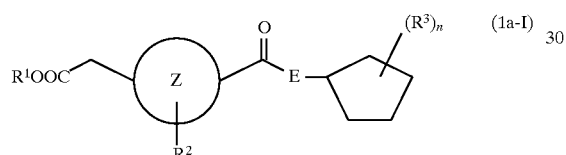 (1a-I)

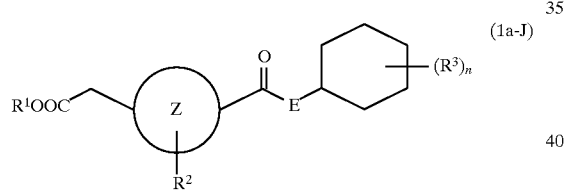 (1a-J)

wherein all the symbols are the same meaning as hereinbefore defined.

More specifically, the compounds of the following formula (Ia-1), (Ia-2), (Ia-3), (Ia-4), (Ia-5), (Ia-6), (Ia-7), (Ia-8), (Ia-9), (Ia-10), (Ia-11), (Ia-12) and non-toxic salts thereof are preferable.

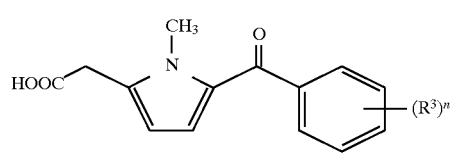 (Ia-1)

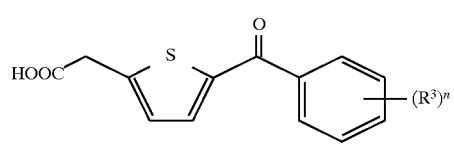 (Ia-2)

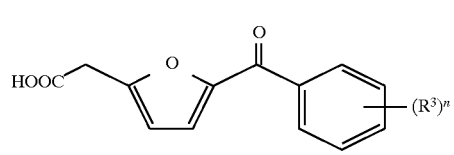 (Ia-3)

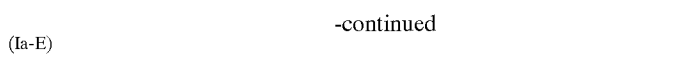 (Ia-4)

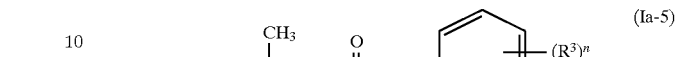 (Ia-5)

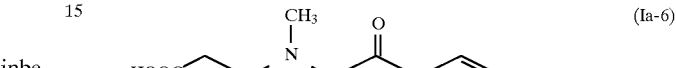 (Ia-6)

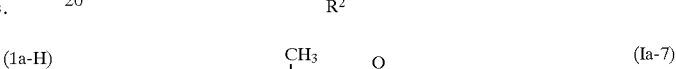 (Ia-7)

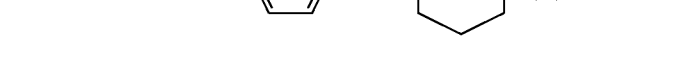 (Ia-8)

 (Ia-9)

 (Ia-10)

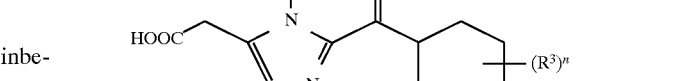 (Ia-11)

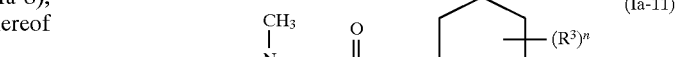 (Ia-12)

wherein all the symbols are the same meaning as hereinbefore defined.

Especially preferable compounds are the compounds described in Example and the following compounds and non-toxic salts thereof.

(1-1)

[Structure: HOOC-CH2-pyrrole(N-CH3)-C(=O)-phenyl-R³]

| R³ | R³ |
|---|---|
| (1) diphenylmethyl | (2) di(4-propylphenyl)methyl |
| (3) 3-pyridinyl | (4) 2-furanyl |
| (5) cyclohexylmethyl | (6) 4-ethylbenzyl |
| (7) 4-methoxybenzyl | (8) 2,2-diphenylethyl |
| (9) 2,2-di(4-propylphenyl)ethyl | (10) diphenylmethyloxy |
| (11) di(4-propylphenyl)methyloxy | (12) 3-pyridinyloxy |
| (13) cyclohexylamino | (14) phenylamino |
| (15) diphenylmethylamino | (16) di(4-propylphenyl)methylamino |
| (17) 3-pyridinylamino | (18) 1-phenylethyloxy |
| (19) 2,2-diphenylethyloxy | (20) 2,2-di(4-propylphenyl)ethyloxy |
| (21) 3-pyridinylmethyloxy | (22) 2-thienylmethyloxy |
| (23) 2-furanylmethyloxy | (24) cyclohexylcarbonyl |
| (25) do(4-propylphenyl)methylcarbobyl | (26) 3-pyridinylcarbonyl |
| (27) 2-thienylcarbonyl | (28) 2-furanylcarbonyl |
| (29) cyclohexylmethyloxymethyl | (30) benzyloxymethyl |
| (31) 2,2-di(4-propylphenyl)ethyloxymethyl | (32) cyclohexylmethylaminomethyl |
| (33) benzylaminomethyl | (34) 2,2-di(4-propylphenyl)ethylaminomethyl |
| (35) cyclohexylmethylcarbonylmethyl | (36) benzylcarbonylmethyl |
| (37) 2,2-di(4-propylphenyl)ethylcarbonylmethyl | (38) diphenylamino |
| (39) dibenzylamino | (40) benzylamino |
| (41) 4-ethylbenzylamino | (42) 1-phenylethylamino |
| (43) 2,2-diphenylethylamino | (44) 2,2-di(4-propylphenyl)ethylamino |
| (45) 3-pyridinylmethylamino | (46) 2-thienylmethylamino |
| (47) 2-furanylmethylamino | (48) 2-cyclohexylethyl |
| (49) 2-cyclohexylethenyl | (50) 2-cyclohexylethynyl |
| (51) 4-methoxycyclohexyl | (52) 4-fluorocyclohexyl |
| (53) 3-nitrocyclohexyl | (54) 4-trifluoromethylphenyl |
| (55) cyclohexyl | (56) phenylthio |
| (57) diphenylmethylthio | (58) phenylthiomethyl |
| (59) diphenylmethylthiomethyl | (60) cyclohexylulfonyl |
| (61) phenylsulfonyl | (62) diphenylsulfonyl |
| (63) cyclohexylsulfonylmethyl | (64) diphenylsulfonylmethyl |
| (65) heptyl | |

(1-2)

[Structure: HOOC-CH2-pyrrole(N-CH3)-C(=O)-R⁰]

| R⁰ | R⁰ |
|---|---|
| (1) 5-indenyl | (2) 1,2,3,4-tetrahydronaphthalen-2-yl |
| (3) 3-(1,2,3,4-tetrahydronaphthalen-2-yl)propyl | (4) 4,5,6,7-tetrahydroinden-5-yl |
| (5) 2,3-dimethyl-4-benzyloxyphenyl | (6) 2,3-dimethyl-4-(1-phenylethyloxy)phenyl |
| (7) cyclopentyl | (8) cycloheptyl |
| (9) 4-phenylcyclopentyl | (10) 4-phenylcycloheptyl |
| (11) 2-chloro-4-pyrrolylphenyl | (12) 2-chloro-4-(2,5-dimethylpyrrolyl)phenyl |

(1-3)

[Structure: HOOC-CH2-pyrrole(N-CH3)-C(=O)-cyclohexyl-R³]

| R³ | R³ |
|---|---|
| (1) cyclohexyl | (2) 4-ethylphenyl |
| (3) 4-methoxyphenyl | (4) pyrrolyl |
| (5) 3-pyridinyl | (6) 2-thienyl |
| (7) 2-furanyl | (8) benzyl |
| (9) phenyloxy | (10) benzyloxy |
| (11) benzoyl | (12) phenylamino |
| (13) benzylamino | (14) diphenylamino |
| (15) phenylcarbonylamino | (16) phenylthiomethyl |
| (17) phenylsulfonylmethyl | (18) 2-cyclohexylmethyl |
| (19) 2-phenylethyl | (20) 2-cyclohexylethenyl |
| (21) 2-phenylethenyl | (22) 2-cyclohexylethenyl |

-continued

| | |
|---|---|
| (23) 2-phenylethynyl | (24) 4-fluorophenyl |
| (25) 3-nitrophenyl | (26) 4-trifluoromethylphenyl |
| (27) 5-bromo-2-thienyl | (28) 2-isoindolinyl |
| (29) benzothiophen-2-yl | (30) heptyl |
| (31) hydrogen | (32) 1,2,3,4-tetrahydronaphthalen-2-yl |
| (33) ethyl | (34) methoxy |
| (35) nitro | (36) fluoro |
| (37) trifluoromethyl | |

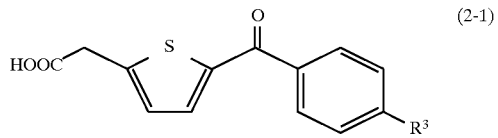

(2-1)

| $R^3$ | $R^3$ |
|---|---|
| (1) cyclohexyl | (2) 4-ethylphenyl |
| (3) 4-methoxyphenyl | (4) diphenylmethyl |
| (5) di(4-propylphenyl)methyl | (6) 3-pyridinyl |
| (7) 2-thienyl | (8) 2-furanyl |
| (9) cyclohexylmethyl | (10) benzyl |
| (11) 4-ethylbenzyl | (12) 4-methoxybenzyl |
| (13) 2,2-diphenylethyl | (14) 2,2-di(4-propylphenyl)ethyl |
| (15) cyclohexyl | (16) 3-pyridinyloxy |
| (17) cyclohexylaino | (18) phenylamino |
| (19) 3-pyridinylamino | (20) 3-pyridinylmethyloxy |
| (21) 2-thienylmethyloxy | (22) 2-furanylmethyloxy |
| (23) cyclohexylcarbonyl | (24) benzoyl |
| (25) di(4-propylphenyl)methylcarbonyl | (26) 3-pyridinylcarbonyl |
| (27) 2-thienylcarbonyl | (28) 2-furanylcarbonyl |
| (29) cyclohexylmethyloxymethyl | (30) cyclohexylmethylaminomethyl |
| (31) cyclohexylmethylcarbonylmethyl | (32) benzylcarbonylmethyl |
| (33) 2,2-di(4-propylphenyl)ethylcarbonylmethyl | (34) diphenylamino |
| (35) 3-pyridinylmethylamino | (36) pyrrolyl |
| (37) 3-pyridinylmethylamino | (38) 2-thienylmethylamino |
| (39) 2-furanylmethylthio | (40) 2-cyclohexylethyl |
| (41) 2-phenylethyl | (42) 2-cyclohexylethenyl |
| (43) 2-phenylethenyl | (44) 2-cyclohexylethynyl |
| (45) 2-phenylethynyl | (46) 4-fluorophenyl |
| (47) 3-nitrophenyl | (48) 4-trifluoromethylphenyl |
| (49) cyclohexylthiomethyl | (50) phenylthiomethyl |
| (51) diphenylmethylthiomethyl | (52) cyclohexylsulfonylmethyl |
| (53) phenylsulfonylmethyl | (54) dipenylsulfonylmetyl |
| (55) 5-bromo-2-thienyl | (56) 2-isoindolinyl |
| (57) benzothiophen-2-yl | (58) heptyl |

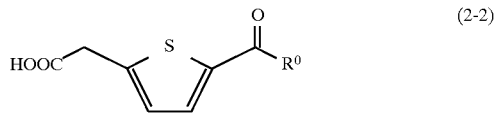

(2-2)

| $R^0$ | $R^0$ |
|---|---|
| (1) 2-naphthyl | (2) 5-indenyl |
| (3) 9-oxofluoren-2-yl | (4) 1,2,3,4-tetrahydronaphthalen-2-yl |
| (5) 3-(1,2,3,4-tetrahydronaphthalen-2-yl)propyl | (6) 4,5,6,7-tetrahydroinden-5-yl |
| (7) 2-methyl-4-benzyloxyphenyl | (8) 2,3-dimethyl-4-benzyloxyphenyl |
| (9) 2,3-dimethyl-4-(1-phenylethyloxy)phenyl | (10) cyclopentyl |
| (11) cycloheptyl | (12) 4-phenylcyclopentyl |
| (13) 4-phenylcycloheptyl | (14) 2-chloro-4-pyrrolylphenyl |
| (15) 2-chloro-4-(2,5-dimethylpyrrolyl)phenyl | |

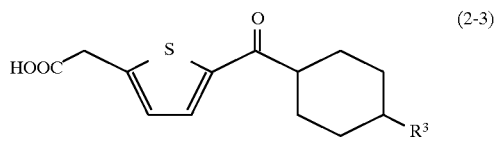

(2-3)

| $R^3$ | $R^3$ |
|---|---|
| (1) cyclohexyl | (2) phenyl |
| (3) 4-ethylphenyl | (4) 4-methoxyphenyl |
| (5) pyrrolyl | (6) 3-pyridinyl |
| (7) 2-thienyl | (8) 2-furanyl |
| (9) benzyl | (10) phenyloxy |

-continued

(11) benzyloxy
(12) benzoyl
(13) phenylamino
(14) benzylamino
(15) diphenylamino
(16) phenylcarbonylamino
(17) phenylthiomethyl
(18) phenylsulfonylmethyl
(19) 2-cyclohexylethyl
(20) 2-phenylethyl
(21) 2-cyclohexylethenyl
(22) 2-enylethenyl
(23) 2-cyclohexylethynyl
(24) 2-phenylethynyl
(25) 4-fluorophenyl
(26) 3-nitrophenyl
(27) 4-trifluoromethylphenyl
(28) 5-bromo-2-thienyl
(29) 2-isoindolinyl
(30) benzothiophen-2-yl
(31) heptyl
(32) hydrogen
(33) 1,2,3,4-tetrahydronaphthalen-2-yl
(34) i-butyl
(35) ethyl
(36) methoxy
(37) nitro
(38) fluoro
(39) trifluoromethyl

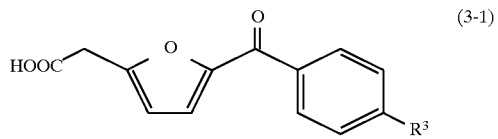

(3-1)

| $R^3$ | $R^3$ |
|---|---|
| (1) cyclohexyl | (2) 4-ethylphenyl |
| (3) 4-methoxyphenyl | (4) diphenylmethyl |
| (5) di(4-propylphenyl)methyl | (6) 3-pyridinyl |
| (7) 2-thienyl | (8) 2-furanyl |
| (9) cyclohexylmethyl | (10) benzyl |
| (11) 4-ethylbenyl | (12) 4-methoxyphenyl |
| (13) 2,2-diphenylethyl | (14) 2,2-di(4-propylphenyl)ethyl |
| (15) cyclohexyloxy | (16) phenyloxy |
| (17) diphenylmethyloxy | (18) di(4-propylphenyl)methyl |
| (19) 3-pyridinyloxy | (20) cyclohexylamino |
| (21) phenylamino | (22) diphenylmethylamino |
| (23) di(4-propylphenyl)methylamino | (24) 3-pyridinylamino |
| (25) benzyloxy | (26) 4-ethylbenzyloxy |
| (27) 1-phenylethyloxy | (28) 2,2-diphenylethyloxy |
| (29) 2,2-di(4-propylphenyl)ethyloxy | (30) 3-pyridinylmethyloxy |
| (31) 2-thienylmethyloxy | (32) 2-furanylmethyloxy |
| (33) cyclohexylcarbonyl | (34) benzoyl |
| (35) di(4-propylphenyl)methylcarbonyl | (36) 3-pyridinylcarbonyl |
| (37) 2-thienylcarbonyl | (38) 2-furanylcarbonyl |
| (39) cyclohexylmethyloxymethyl | (40) benzyloxymethyl |
| (41) 2,2-di(4-propylphenyl)ethyloxymethyl | (42) cyclohexylmethylaminomethyl |
| (43) benzylaminomethyl | (44) 2,2-di(4-propylphenyl)ethylaminomethyl |
| (45) cyclohexylmethylcarbonylmethyl | (46) benzylcarbonylmethyl |
| (47) 2,2-di(4-propylphenyl)ethylcarbonylmethyl | (48) diphenylamino |
| (49) dibenzylamino | (50) phenylcarbonylamino |
| (51) pyrrolyl | (52) benzylamino |
| (53) 4-ethylbenzylamino | (54) 1-phenylethylamino |
| (55) 2,2-diphenylethylamino | (56) 2,2-di(4-propylphenyl)ethylamino |
| (57) 3-pyridinylmethylamino | (58) 2-thienylmethylamino |
| (59) 2-furanylmethylamino | (60) 2-cyclohexylethyl |
| (61) 2-phenylethyl | (62) 2-cyclohexylethenyl |
| (63) 2-phenylethenyl | (64) 2-cyclohexylethynyl |
| (65) 2-phenylethynyl | (66) 4-fluorophenyl |
| (67) 3-nitrophenyl | (68) 4-trifluoromethylphenyl |
| (69) cyclohexylthiomethyl | (70) phenylthiomethyl |
| (71) diphenylmethylthiomethyl | (72) cyclohexylsulfonylmethyl |
| (73) phenylsulfonylmethyl | (74) diphenylsulfonylmethyl |
| (75) 5-bromo-2-thienyl | (76) 2-isoindolinyl |
| (77) benzothiophen-2-yl | (78) heptyl |

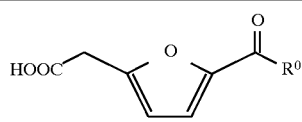

(3-2)

| $R^0$ | $R^0$ |
|---|---|
| (1) 2-naphthyl | (2) 5-indenyl |
| (3) 9-oxofluoren-2-yl | (4) 1,2,3,4-tetrahydronaphthalen-2-yl |
| (5) 3-(1,2,3,4-tetrahydronaphthalen-2-yl)propyl | (6) 4,5,6,7-tetrahydroinden-5-yl |
| (7) 2-methyl-4-benzyloxyphenyl | (8) 2,3-demethyl-4-benzyloxyphenyl |
| (9) 2,3-dimethyl-4-(1-phenylethyloxy)phenyl | (10) cyclopentyl |
| (11) cycloheptyl | (12) 4-phenylcyclopentyl |

-continued

(13) 4-phenylcycloheptyl  
(15) 2-chloro-4-(2,5-dimethylpyrrolyl)phenyl

(14) 2-chloro-4-pyrrolyphenyl

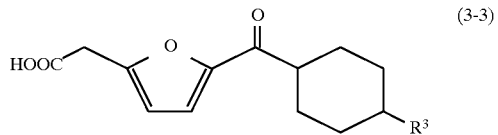

(3-3)

| R³ | R³ |
|---|---|
| (1) cyclohexyl | (2) phenyl |
| (3) 4-ethylphenyl | (4) 4-methoxyphenyl |
| (5) pyrrolyl | (6) 3-pyridinyl |
| (7) 2-thienyl | (8) 2-furanyl |
| (9) benzyl | (10) phenyloxy |
| (11) benzyloxy | (12) benzoyl |
| (13) phenylamino | (14) benzylamino |
| (15) diphenylamino | (16) phenylcarbonylamino |
| (17) phenylthiomethyl | (18) phenylsulfonylmethyl |
| (19) 2-cyclohexylethyl | (20) 2-phenylethyl |
| (21) 2-cyclohexylethenyl | (22) 2-phenylethenyl |
| (23) 2-cyclohexylethynyl | (24) 2-phenylethynyl |
| (25) 4-fluorophenyl | (26) 3-nitrophenyl |
| (27) 4-trifluoromethylphenyl | (28) 5-bromo-2-thienyl |
| (29) 2-isoindolinyl | (30) benzothiophen-2-yl |
| (31) heptyl | (32) hydrogen |
| (33) 1,2,3,4-tetrahydronaphthalen-2-yl | (34) t-butyl |
| (35) ethyl | (36) methoxy |
| (37) nitro | (38) fluoro |
| (39) trifluoromethyl | |

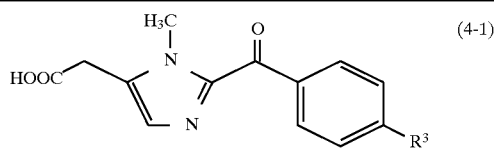

(4-1)

| R³ | R³ |
|---|---|
| (1) cyclohexyl | (2) 4-ethylphenyl |
| (3) 4-methoxyphenyl | (4) diphenylmethyl |
| (5) di(4-propylphenyl)methyl | (6) 3-pyridinyl |
| (7) 2-thienyl | (8) 2-furanyl |
| (9) cyclohexylmethyl | (10) benzyl |
| (11) 4-ethylbenzyl | (12) 4-methoxybenzyl |
| (13) 2,2-diphenylethyl | (14) 2,2-di(4-propylphenyl)ethyl |
| (15) cyclohexyloxy | (16) phenyloxy |
| (17) diphenylmethyloxy | (18) di(4-propylphenyl)methyloxy |
| (19) 3-pyridinyloxy | (20) cyclohexylamino) |
| (21) phenylamino | (22) diphenylmethylamino |
| (23) di(4-propylphenyl)methylamino | (24) 3-pyridinylamino |
| (25) benzyloxy | (26) 4-ethylbenzyloxy |
| (27) 1-phenylethyloxy | (28) 2,2-diphenylethyloxy |
| (29) 2,2-di(4-propylphenyl)ethyloxy | (30) 3-pyridinylmethyloxy |
| (31) 2-thienylmethyloxy | (32) 2-furanylmethyloxy |
| (33) cyclohexylcarbonyl | (34) benzoyl |
| (35) di(4-propylphenyl)methylcarbonyl | (36) 3-pyridinylcarbonyl |
| (37) 2-thienylcarbonyl | (38) 2-furanylcarbonyl |
| (39) cyclohexylmethyloxymethyl | (40) benzyloxymethyl |
| (41) 2,2-di(4-propylphenyl)ethyloxymethyl | (42) cyclohexylmethylaminomethyl |
| (43) benzylaminomethyl | (44) 2,2-di(4-propylphenyl)ethylaminomethyl |
| (45) cyclohexylmethylcarbonylmethyl | (46) benzylcarbonylmethyl |
| (47) 2,2-di(4-propylphenyl)ethylcarbonlmethyl | (48) diphenylamino |
| (49) dibenzylamino | (50) phenylcarbonylamino |
| (51) pyrrolyl | (52) benzylamino |
| (53) 4-ethylbenzylamino | (54) 1-phenylethylamino |
| (55) 2,2-diphenylethylamino | (56) 2,2-di(4-propylphenyl)ethylamino |
| (57) 3-pyrindinylmethylamino | (58) 2-thienylmethylamino |
| (59) 2-furanylmethylamino | (60) 2-cyclohexylethyl |
| (61) 2-phenylethyl | (62) 2-cyclohexylethenyl |
| (63) 2-phenylethenyl | (64) 2-cyclohexylethynyl |
| (65) 2-phenylethynyl | (66) 4-fluorophenyl |
| (67) 3-nitrophenyl | (68) 4-trifluoromethylphenyl |
| (69) cyclohexylthiomethyl | (70) phenylthiomethyl |
| (71) diphenylmethylthiomethyl | (72) cyclohexylsullfonylmethyl |
| (73) phenylsulfonylmethyl | (74) diphenylsulfonylmethyl |

| | |
|---|---|
| (75) 5-bromo-2-thienyl | (76) 2-isoindolinyl |
| (77) benzothiophen-2-yl | (78) heptyl |

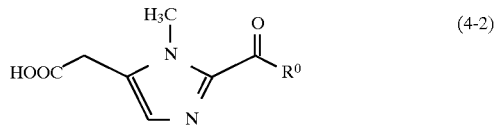

| $R^0$ | $R^0$ |
|---|---|
| (1) 2-naphthyl | (2) 5-indenyl |
| (3) 9-oxofluoren-2-yl | (4) 1,2,3,4-tetrahydronaphthalen-2-yl |
| (5) 3-(1,2,3,4-tetrahydronaphthalen-2-yl)propyl | (6) 4,5,6,7-tetrahydroinden-5-yl |
| (7) 2-methyl-4-benzyloxyphenyl | (8) 2,3-dimethyl-4-benzyloxyphenyl |
| (9) 2,3-dimethyl-4-(1-phenylethyloxy)phenyl | (10) cyclopentyl |
| (11) cycloheptyl | (12) 4-phenylcyclopentyl |
| (13) 4-phenylcycloheptyl | (14) 2-chloro-4-pyrrolylphenyl |
| (15) 2-chloro-4-(2,5-dimethylpyrrolyl)phenyl | |

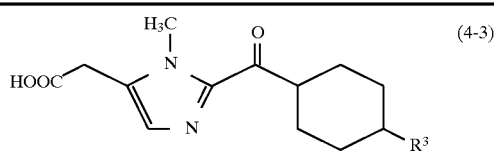

| $R^3$ | $R^3$ |
|---|---|
| (1) cyclohexyl | (2) phenyl |
| (3) 4-ethylphenyl | (4) 4-methoxyphenyl |
| (5) pyrrolyl | (6) 3-pyridinyl |
| (7) 2-thienyl | (8) 2-furanyl |
| (9) benzyl | (10) phenyloxy |
| (11) benzyloxy | (12) benzoyl |
| (13) phenylamino | (14) benzylamino |
| (15) diphenylamino | (16) phenylcarbonylamino |
| (17) phenylthiomethyl | (18) phenylsulfonylmethyl |
| (19) 2-cyclohexylethyl | (20) 2-phenylethyl |
| (21) 2-cyclohexylethenyl | (22) 2-phenylethenyl |
| (23) 2-cyclohexylethynyl | (24) 2-phenylethynyl |
| (25) 4-fluorophenyl | (26) 3-nitrophenyl |
| (27) 4-trifluoromethylphenyl | (28) 5-bromo-2-thienyl |
| (29) 2-isoindolinyl | (30) benzothiophen-2-yl |
| (31) heptyl | (32) hydrogen |
| (33) 1,2,3,4-tetrahydronaphthalen-2-yl | (34) t-butyl |
| (35) ethyl | (36) methoxy |
| (37) nitro | (38) fluoro |
| (39) trifluoromethyl | |

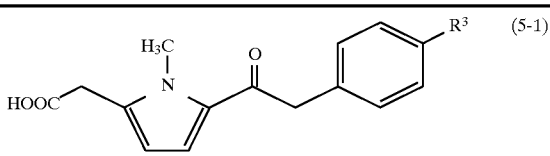

| $R^3$ | $R^3$ |
|---|---|
| (1) cyclohexyl | (2) 4-ethylphenyl |
| (3) 4-methoxyphenyl | (4) diphenylmethyl |
| (5) di(4-propylphenyl)methyl | (6) 3-pyridinyl |
| (7) 2-thienyl | (8) 2-furanyl |
| (9) cyclohexylmethyl | (10) benzyl |
| (11) 4-ethylbenzyl | (12) 4-methoxybenzyl |
| (13) 2,2-diphenylethyl | (14) 2,2-di(4-propylphenyl)ethyl |
| (15) cyclohexyloxy | (16) phenyloxy |
| (17) diphenylmethyloxy | (18) di(4-propylphenyl)methyloxy |
| (19) 3-pyridinyloxy | (20) cyclohexylamino |
| (21) phenylamino | (22) diphenylmethylamino |
| (23) di(4-propylphenyl)methylamino | (24) 3-pyridinylamino |
| (25) benzyloxy | (26) 4-ethylbenzyloxy |
| (27) 1-phenylethyloxy | (28) 2,2-diphenylethyloxy |
| (29) 2,2-di(4-propylphenyl)ethyloxy | (30) 3-pyridinylmethyloxy |
| (31) 2-thienylmethyloxy | (32) 2-furanylmethyloxy |
| (33) cyclohexylcarbonyl | (34) benzoyl |
| (35) di(4-propylphenyl)methylcarbonyl | (36) 3-pyridinylcarbonyl |
| (37) 2-thienylcarbonyl | (38) 2-furanylcarbonyl |

-continued

| | |
|---|---|
| (39) cyclohexylmethyloxymethyl | (40) benzyloxymethyl |
| (41) 2,2-di(4-propylphenyl)ethyloxymethyl | (42) cyclohexylmethylaminomethyl |
| (43) benzylaminomethyl | (44) 2,2-di(4-propylphenyl)ethylaminomethyl |
| (45) cyclohexylmethylcarbonylmethyl | (46) benzylcarbonylmethyl |
| (47) 2,2-di(4-propylphenyl)ethylcarbonylmethyl | (48) diphenylamino |
| (49) dibenzylamino | (50) phenylcarbonylamino |
| (51) pyrrolyl | (52) benzylamino |
| (53) 4-ethylbenzylamino | (54) 1-phenylethylamino |
| (55) 2,2-diphenylethylamino | (56) 2,2-di(4-propylphenyl)ethylamino |
| (57) 3-pyrdidinylmethylamino | (58) 2-thienylmethylamino |
| (59) 2-furanylmethylamino | (60) hydrogen |
| (61) 2-cyclohexylethyl | (62) 2-phenylethyl |
| (63) 2-cyclohexylethenyl | (64) 2-phenylethenyl |
| (65) 2-cyclohexylethynyl | (66) 2-phenylethynyl |
| (67) 4-fluorophenyl | (68) 3-nitrophenyl |
| (69) 4-trifluoromethylphenyl | (70) cyclohexylthiomethyl |
| (71) phenylthiomethyl | (72) diphenylmethylthiomethyl |
| (73) cyclohexylsulfonylmethyl | (74) phenylsulfonylmethyl |
| (75) diphenylsulfonylmethyl | (76) 5-bromo-2-thienyl |
| (77) 2-isoindolinyl | (78) benzothiophen-2-yl |
| (79) heptyl | |

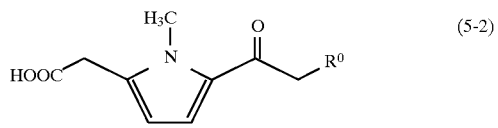

(5-2)

| $R^0$ | $R^0$ |
|---|---|
| (1) 2-naphthyl | (2) 5-indenyl |
| (3) 9-oxofluoren-2-yl | (4) 1,2,3,4-tetrahydronaphthalen-2-yl |
| (5) 3-(1,2,3,4-tetrahydronaphthalen-2-yl)propyl | (6) 4,5,6,7-tetrahydroinden-5-yl |
| (7) 2-methyl-4-benzyloxyphenyl | (8) 2,3-dimethyl-4-benzyloxyphenyl |
| (9) 2,3-dimethyl-4-(1-phenylethyloxy)phenyl | (10) cyclopentyl |
| (11) cycloheptyl | (12) 4-phenylcyclopentyl |
| (13) 4-phenylcycloheptyl | (14) 2-chloro-4-pyrrolylphenyl |
| (15) 2-chloro-4-(2,5-dimethylpyrrolyl)phenyl | |

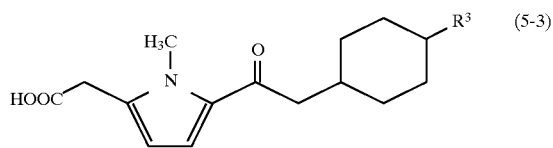

(5-3)

| $R^3$ | $R^3$ |
|---|---|
| (1) cyclohexyl | (2) phenyl |
| (3) 4-ethylphenyl | (4) 4-methoxyphenyl |
| (5) pyrrolyl | (6) 3-pyridinyl |
| (7) 2-thienyl | (8) 2-furanyl |
| (9) benzyl | (10) phenyloxy |
| (11) benzyloxy | (12) benzoyl |
| (13) phenylamino | (14) benzylamino |
| (15) diphenylamino | (16) phenylcarbonylamino |
| (17) phenylthiomethyl | (18) phenylsulfonylmethyl |
| (19) 2-cyclohexylethyl | (20) 2-phenylethyl |
| (21) 2-cyclohexylethenyl | (22) 2-phenylethenyl |
| (23) 2-cyclohexylethynyl | (24) 2-phenylethynyl |
| (25) 4-fluorophenyl | (26) 3-nitrophenyl |
| (27) 4-trifluoromethylphenyl | (28) 5-bromo-2-thienyl |
| (29) 2-isoindolinyl | (30) benzothiophen-2-yl |
| (31) heptyl | (32) hydrogen |
| (33) 1,2,3,4-tetrahydronaphthalen-2-yl | (34) t-butyl |
| (35) ethyl | (36) methoxy |
| (37) nitro | (38) fluoro |
| (39) trifluoromethyl | |

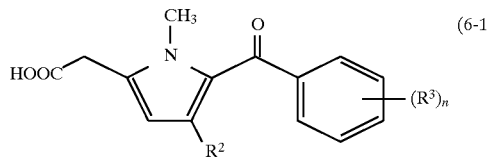

(6-1)

| No. | R² | (R³)ₙ | No. | R² | (R³)ₙ |
|---|---|---|---|---|---|
| (1) | hydrogen | 4-methyl | (2) | hydrogen | 4-t-butyl |
| (3) | hydrogen | 4-chloro | (4) | hydrogen | 4-methoxy |
| (5) | hydrogen | 4-nitro | (6) | hydrogen | 4-methylthio |
| (7) | hydrogen | 4-trifluoromethyl | (8) | hydrogen | 4-cyano |
| (9) | hydrogen | 4-fluoro | (10) | hydrogen | 3,5-di-t-butyl |
| (11) | methyl | 4-t-butyl | (12) | methyl | 4-chloro |
| (13) | methyl | 4-methyl | (14) | methyl | 3,5-di-t-butyl |
| (15) | hydrogen | 4-isobutyl | (16) | hydrogen | 4-bromo |
| (17) | hydrogen | 4-iodo | (18) | hydrogen | 4-hexyloxy |
| (19) | hydrogen | 4-isopropyloxy | | | |

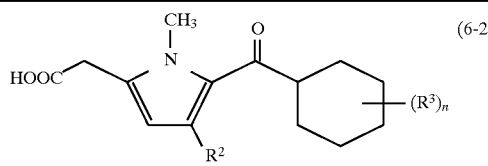

(6-2)

| No. | R² | (R³)ₙ | No. | R² | (R³)ₙ |
|---|---|---|---|---|---|
| (1) | hydrogen | 4-methyl | (2) | hydrogen | 4-t-butyl |
| (3) | hydrogen | 4-chloro | (4) | hydrogen | 4-methoxy |
| (5) | hydrogen | 4-nitro | (6) | hydrogen | 4-methylthio |
| (7) | hydrogen | 4-trifluoromethyl | (8) | hydrogen | 4-cyano |
| (9) | hydrogen | 4-fluoro | (10) | hydrogen | 3,5-di-t-butyl |
| (11) | methyl | 4-t-butyl | (12) | methyl | 4-chloro |
| (13) | methyl | 4-methyl | (14) | methyl | 3,5-di-t-butyl |
| (15) | hydrogen | 4-isobutyl | (16) | hydrogen | 4-bromo |
| (17) | hydrogen | 4-iodo | (18) | hydrogen | 4-hexyloxy |

In the present invention, it is able to formulate using each active ingredient or combination of more than two active ingredients.

Unless otherwise specified, all isomers are included in the invention. For example, alkyl, alkoxy, alkenylene and alkylene includes straight and branched ones. Double bond in alkenylene includes E, Z and EZ mixture. Isomers generated by asymmetric carbon(s) e.g. branched alkyl are included in the present invention.

Salts

The compounds of the formula (Ia) and (Ib) of the present invention may be converted into the corresponding salts. Non-toxic and water-soluble salts are preferable. Suitable salts, for example, are as follows:
salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

The compounds of the formula (Ia) and (Ib) may be converted into the corresponding acid addition salts. Non-toxic and water-soluble salts are preferable. Suitable salts, for example, are as follows: salts of inorganic acids e. g. hydrochloride, hydrobromide, hydroiodide, sulfate, phosphate, nitrate; salts of organic acids e. g. acetate, lactate, tartarate, benzoate, citrate, methanesulphonate, ethanesulphonate, benzenesulphonate, toluenesulphonate, isedthioate, glucuronate, gluconate.

Process for the preparation

A compound of the formula (Ic):

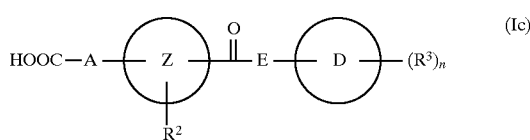

(Ic)

wherein all the symbols are the same meaning as hereinbefore defined, in a compound of the present invention of the formula (Ia), may be prepared:

(1) by hydrolyzing an ester of the formula (Id):

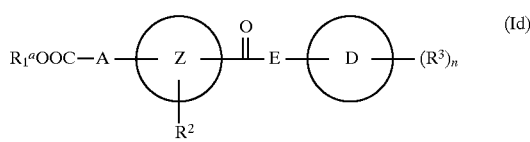

(Id)

wherein $R_1^a$ is C1–4 alkyl and the other symbols are the same meaning as hereinbefore defined, or (2) by hydrolyzing a compound of the formula (II):

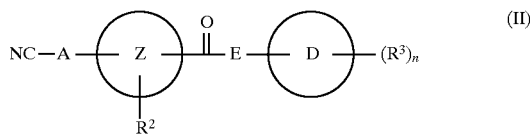

(II)

wherein all the symbols are the same meaning as hereinbefore defined.

The compound of the formula (Id) among the compounds of the present invention, may be prepared:

(3) by reacting a compound of the formula (III):

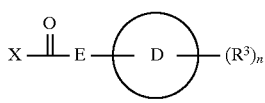

wherein X is halogen, the other symbols are the same meaning as hereinbefore defined, with a compound of the formula (IV)

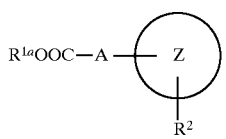

wherein all the symbols are the same meaning as hereinbefore defined.

Compounds of the formula (Ia) wherein $R^4$ is hydrogen and /or $R^7$ is hydrogen, may be prepared:

(i) by using a compound of the formula (III) and (IV) wherein hydrogen represented by $R^4$ and $R^7$ is replaced by benzyloxycarbonyl (protecting group) as a staring material, (ii) by reacting above compounds, (iii) by hydrolyzing a compound obtained in above reaction (ii) using an acid (hydrochloric acid, trifluoroacetic acid etc.), (iv) by hydrolyzing a compound obtained in above reaction (iii) using an aqueous solution of an alkaline (potassium hydroxide, sodium hydroxide, potassium carbonate, sodium carbonate etc.).

The reaction (1) is known, for example, it may be carried out in water miscible organic solvent (methanol, ethanol, isopropanol, tetrahydrofuran(THF), dioxane or two or more of the mixture, etc.), using an aqueous solution of an alkaline (potassium hydroxide, sodium hydroxide, potassium carbonate, sodium carbonate etc.) at −10°~50° C.

The reaction (2) is known, for example, it may be carried out in water miscible organic solvent (methanol, ethanol, isopropanol, tetrahydrofuran(THF), dioxane or two or more of the mixture, etc.), using an aqueous solution of an alkaline (potassium hydroxide, sodium hydroxide, potassium carbonate, sodium carbonate etc.) at 40°~150° C.

The reaction (3) is known, for example, it may be carried out in organic solvent (xylene, chloroform, methylene chloride, THF, toluene, acetonitrile etc.), in the presence or absence of Lewis acid (aluminum chloride, iron(III) chloride, boron trifluoride diethyl etherate etc.) or an base (triethylamine, pyridine etc.) at 20°~150° C.

Starting materials and reagents

The starting materials and reagents in the present invention are known per se or may be prepared by known methods.

For example, a compound of the formula (II) may be prepared by using a reaction depicted in following scheme:

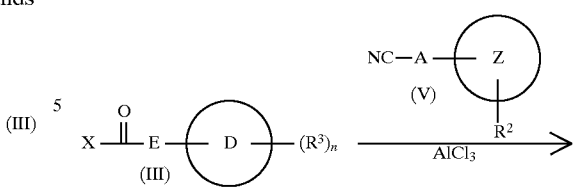

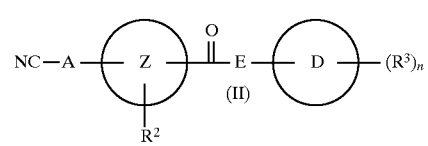

wherein all the symbols are the same meaning as hereinbefore defined.

For example, a compound included in the formula (III) of the formula:

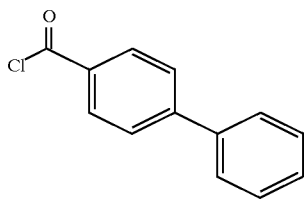

is on the market.

For example, a compound included in the formula (IV) of the formula:

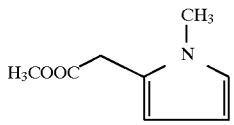

is on the market.

For example, a compound included in the formula (V) of the formula:

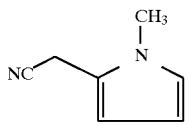

is on the market.

Pharmacological Activities

A compound of the formula (Ia) of the present invention possess an inhibitory activity on 5α-reductase and therefore are useful for prevention and/or treatment of diseases induced by the excess generation of dihydrotestosterone in mammals, especially human. The diseases such as above, for example, are alopecia (e.g. androgenic alopecia), acnes, hypertrophy of prostate and prostatic cancer. An inhibitory activity on 5α-reductase of the present invention is confirmed by the screening system described hereafter (1) Preparation of 5α-reductase from human prostates Frozen human prostates were thawed on ice and minced with scissors into small pieces (~1 mm³). The minced tissue was homogenized in 3 tissue volumes of ice cold medium A (20 mM potassium phosphate, pH 6.5, containing 0.32M sucrose, 1 mM dithiothreitol, 50 μM NADPH, 1 mM EDTA), first with a Brinkmann Polytron and then with a Dounce homogenizer. The homogenate was filtered through gauze and the filtrate was centrifuged at 140,000×g at 4° C. for 60 min. The resulting pellet was washed with 3 tissue volumes of medium A. The washed pellet was suspended (5–10 mg protein/ml) in 20 mM potassium phosphate, pH 6.5, containing 20% glycerol, 50 μM NADPH and 1 mM dithiothreitol. An appropriate aliquot of this suspension was used as the source of 5α-reductase.

(2) Assay

5α-reductase activity was determined by following the conversion of testosterone to 5α-dihydrotestosterone (DHT). In brief, buffer (100 mM Tris-citrate, pH5.0), 1 mM NADPH and human prostatic 5α-reductase (0.4–1 mg protein) were placed in test tubes. After addition of test compounds (dissolved in 5 μl in DMSO or EtOH) or solvents to the tubes, the solutions were preincubated at room temperature for 10 min. The reactions were initiated by addition of 1 μM $^{14}$C-testosterone to a final volume of 0.5 ml. Following 30 min incubation at 37° C., the reactions were stopped by addition of 5 ml dichloromethane. After centrifugation at 1000 rpm for 5 min, the organic phase (bottom) was collected and the volume reduced to ~100 μl in a 42° C. water bath. The solutions were applied to silica plates and the plates were developed in chloroform/ethyl acetate (3:1) at room temperature. The radioactivity profiles were determined by a BIOSCAN imaging scanner. The silica in sections identified by BIOSCAN and counted in a scintillation counter. Enzyme activity was calculated from the percent of recovered radio label converted to the product DHT.

The results are shown in the table 1 and 2.

TABLE 1

| Ex.No. | IC$_{50}$ (μM) |
|---|---|
| 2 | 0.024 |
| 3(1) | 0.020 |
| 3(2) | 0.019 |
| 3(5) | 0.21 |
| 3(8) | 0.024 |
| 3(16) | 0.17 |
| 3(18) | 0.45 |
| 3(20) | 0.13 |
| 3(22) | 0.84 |
| 3(41) | 0.098 |
| 3(47) | 0.056 |
| 3(50) | 0.16 |
| 3(54) | 0.023 |
| 3(55) | 0.024 |
| 3(62) | 0.041 |
| 3(70) | 0.17 |
| 3(77) | 0.25 |
| 3(82) | 0.63 |
| 3(83) | 0.092 |

TABLE 2

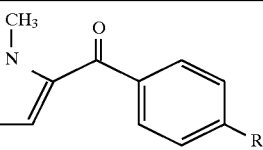

| R | IC$_{50}$ (μM) |
|---|---|
| methyl | 8.0 |
| t-butyl | 0.4 |
| iodo | 0.44 |
| hexyloxy | 0.17 |
| isobutyl | 0.074 |

Toxicity

The toxicity of a compound of the present invention of the formula (Ia) are very low and therefore, it may be estimated to be safe for pharmaceutical use.

Application for Pharmaceuticals

A compound of the present invention of the formula (Ia) and non-toxic salts thereof are useful for 5α-reductase inhibitors.

5α-Reductase inhibitors are useful for prevention and/or treatment of diseases induced by the excess generation of dihydrotestosterone in mammals, especially human. The diseases such as above, for example, are alopecia (e.g. androgenic alopecia), acnes, hypertrophy of prostate and prostatic cancer.

For the purpose above described, the compounds of the formula (Ia) and (Ib), of the present invention and non-toxic salts thereof may be normally by administered systemically or locally usually by oral or parenteral administration.

The doses to be administered are determined depending upon age, body weight, symptom, the desired therapeutic effect, the route of administration, and the duration of the treatment etc. In the human adult, the doses per person are generally between 1 mg and 1000 mg, by oral administration, up to several times per day, and between 100 μg and 100 mg, by parenteral administration (preferable intravenous administration), up to several times per day, or continuous administration between 1 and 24 hrs. per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules.

Capsules include hard capsules and soft capsules.

In such compositions, one or more of the active compound(s) is or are admixed with at least one inert diluent (such as lactose, mannitol, mannit, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents, and assisting agents for dissolving such as glutamic acid, aspartic acid etc.).

The tablets or pills may, if desired, be coated with a film of gastric or enteric material (such as sugar, gelatin, hydroxypropyl cellulose or hydroxypropylmethyl cellulose phthalate, etc.), or be coated with more than two films. And further, coating may include containment within capsules of absorbable materials such as gelatin.

Liquid compositions for oral administration include pharmaceutically-acceptable emulsions, solutions, syrups and elixirs. In such compositions, one or more of the active compound(s) is or are contained in inert diluent(s) commonly used in the art (purified water, ethanol etc.). Besides inert diluents, such compositions may also comprise adjuvants (such as wetting agents, suspending agents, etc.), sweetening agents, flavouring agents, perfuming agents, and preserving agents.

Other compositions for oral administration included spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. No. 2,868,691 or 3,095,355 may be used.

Injections for parenteral administration include sterile aqueous or non-aqueous solutions, suspensions and emulsions. Aqueous solutions, suspensions include distilled water for injection and physiological salt solution. Non-aqueous solutions, suspensions include propylene glycol, polyethylene glycol, vegetable oil such as olive oil, alcohol such as ethanol, POLYSORBATE80 (registered trade mark), etc.

Injections may comprise additional other than inert diluents: e.g. preserving agents, wetting agents, emulsifying agents, dispersing agents, stabilizing agent, assisting agents such as assisting agents for dissolving (glutamic acid, aspartic acid, etc.).

They may be sterilized for example, by filtration through a bacteria-retaining filter, by incorporation of sterilizing agents in the compositions or by irradiation. They may also be manufactured in the form of sterile solid compositions and which may be dissolved in sterile water or some other sterile diluent(s) for injection immediately before used.

Other compositions for parenteral administration include liquids for external use, and endermic liniments, ointment, suppositories for rectal administration and pessaries for vaginal administration which comprise one or more of the active compound(s) and may be prepared by per se known methods.

Compositions for dermal administration; especially for the treatment and prevention of alopecia and acne, include liquids for external use such as lotions, tonics, sprays, solutions, suspensions, emulsions and liniments such as ointments, gels and creams.

Such compositions may comprise one or more active ingredient(s) and at least one inert diluent(s), for example, distilled water, a lower alcohol such as ethanol, a higher alcohol such as cetanol, a poly alcohol such as polyethylene glycol, propylene glycol, a cellulose derivative such as hydroxypropyl cellulose, animal or plant fats, petroleum jelly (e.g. as sold under the Trademark "VASELINE"), wax, silicone, a vegetable oil, such as olive oil, a surfactant, or zinc oxide.

Besides inert diluents, such compositions may also comprise adjuvants (e.g. wetting agents, suspending agents, perfuming agents, preserving agents).

REFERENCE EXAMPLE AND EXAMPLE

The following examples illustrate the present invention, but not limit the present invention.

The solvents in the parentheses show the developing or eluting solvents and the rations of the solvents used are by volume in chromatographic separations.

Unless otherwise specified, "NMR" was measured in a d-chloroform (CDCl₃) solution and "IR" was measured by the KBr disk method respectively.

Reference example 1

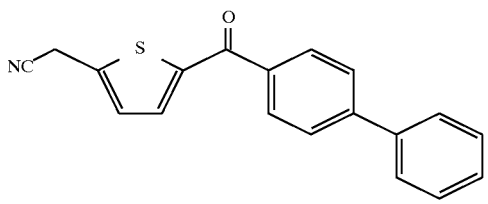

To a mixture of 15.0 g of aluminum chloride in 100 ml of chloroform was added 10.9 g of 4-biphenyl carbonyl chloride. Slowly, 5.3 ml of 2-thiophenylacetonitrile was added to the mixture. The precipitate which formed was broken up, and the mixture was heated to reflux. After approximately four hours, heating was stopped. The mixture was then poured onto ice, and 300 ml of chloroform followed by 50 ml of conc. hydrochloric acid was added. The mixture was stirred to break up as much residue as possible. The organic layer separated was washed with dilute hydrochloric acid, followed by dilute sodium bicarbonate solution, dried over anhydrous potassium carbonate, and filtered. The filtrate was concentrated and purified on silica gel chromatography to obtain after trituration with ether 3.7 g of the desired product.

mp=181°–183° C.

NMR: $\delta$3.99 (s, 2H), 7.17 (d, 1H), 7.36–7.77 (m, 8H), 7.87–7.98 (m, 2H).

Example 1

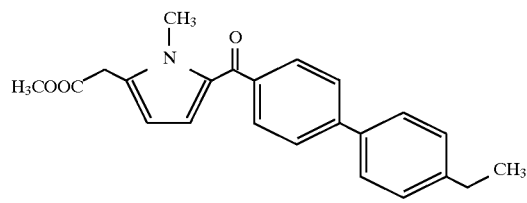

To a solution of 2.26 g of 4'-ethyl-4-biphenyl carboxylic acid in 50.0 ml of chloroform was added 1.0 ml of oxalyl chloride, followed by two drops of dimethylformamide. The mixture was heated to reflux with the exclusion of moisture. After a period of one hour, the mixture was concentrated. To the concentrate was added 1.53 g of methyl 1-methyl-2-pyrroleacetate and 20.0 ml of anhydrous m-xylene. The mixture was again heated to reflux with the exclusion of moisture. After a period of 24 hours, heating was stopped. The mixture was then concentrated, taken up in chloroform, washed with dilute sodium hydroxide solution, dried over potassium carbonate, and concentrated. This concentrate was purified on silica gel eluted with chloroform to yield 1.47 g of the desired product.

mp=124°–126° C.

NMR: $\delta$1.28 (t, 3H), 2.71 (q, 2H), 3.73 (s, 2H), 3.75 (s, 3H), 3.97 (s, 3H), 6.13 (d, 1H), 6.74 (d, 1H), 7.30 (d, 2H), 7.51–7.70 (m, 4H), 7.87 (d, 2H).

Example 2

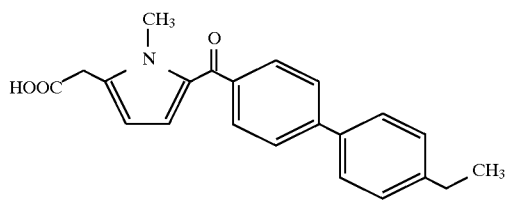

To a solution of 1.25 g of the compound obtained in example 1 in 90.0 ml of methanol was added 7.0 ml of 1.0N sodium hydroxide solution, and the mixture was stirred overnight. The mixture was then concentrated. The concentrate was taken up in warm water, treated with 10.0 ml of 1.0N hydrochloric acid, and extracted with chloroform. The organic extract was dried over anhydrous magnesium sulfate, and filtered. The filtrate was concentrated, and triturated in ether-hexane to yield 1.0 g of the desired product.

mp=194°–196° C.

NMR: δ1.29 (t, 3H), 2.72 (q, 2H), 3.80 (s, 2H), 3.99 (s, 3H), 6.18 (d, 1H), 6.77 (d, 1H), 7.31 (d, 2H), 7.51–7.72 (m, 4H), 7.88 (d, 2H).

IR: ν3020, 1694, 1628, 1600, 1481, 1458, 1380, 1267, 1239, 1194 cm$^{-1}$.

Example 3(1)–3(93)

The following compounds were obtained by the same procedure as a series of reaction of example 1→example 2, using a corresponding carboxylic acid or the compound of reference example 1 or a corresponding nitrile compound instead of 4'-ethyl-4-biphenyl carboxylic acid and a corresponding compound instead of methyl 1-methyl-2-pyrroleacetate in example 1.

Example 3(1)

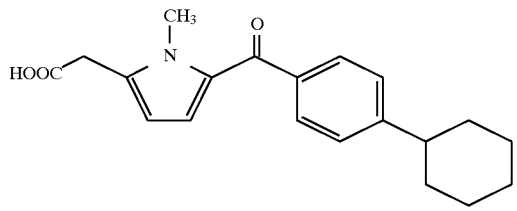

NMR: δ1.43 (m, 5H), 1.87 (m, 5H), 2.58 (m, 1H), 3.77 (s, 2H), 3.95 (s, 3H), 6.15 (d, 1H), 6.70 (d, 1H), 7.26 (d, 2H), 7.72 (d, 2H).

IR: ν2925, 1696, 1609, 1481, 1453, 1375, 1262, 886, 756 cm$^{-1}$.

Example 3(2)

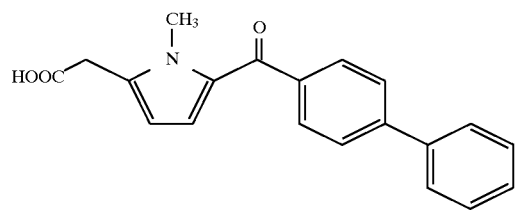

NMR: δ3.79 (s, 2H), 3.99 (s, 3H), 6.17 (d, 1H), 6.76 (d, 1H), 7.34–7.53 (m, 3H), 7.60–7.72 (m, 4H), 7.85–7.93 (m, 2H).

IR: ν3030, 1715, 1624, 1603, 1488, 1456, 1378, 1266 cm$^{-1}$.

Example 3(3)

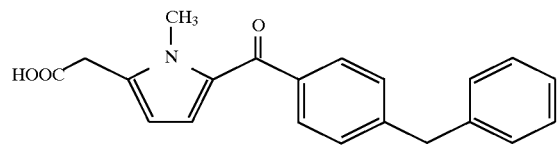

NMR: δ3.77 (s, 2H), 3.96 (s, 3H), 4.06 (s, 2H), 6.14 (d, 1H), 6.69 (d, 1H), 7.14–7.40 (m, 7H), 7.67–7.80 (m, 2H).

IR: ν3030, 1711, 1628, 1481, 1455, 1371, 1265, 1231 cm$^{-1}$.

Example 3(4)

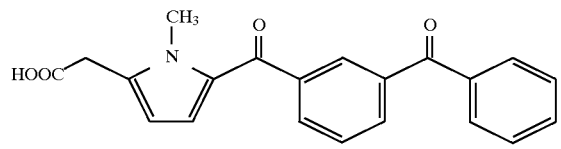

NMR: δ3.78 (s, 2H), 3.98 (s, 3H), 6.15 (d, 1H), 6.70 (d, 1H), 7.42–7.63 (m, 4H), 7.79 (d, 2H), 7.96 (m, 2H), 8.16 (s, 1H).

IR: ν3060, 1705, 1654, 1629, 1487, 1453, 1377, 1252 cm$^{-1}$

Example 3(5)

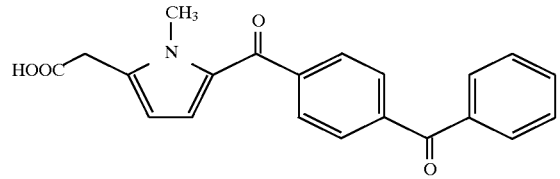

NMR: δ3.79 (s, 2H), 4.00 (s, 3H), 6.18 (d, 1H), 6.71 (d, 1H), 7.42–7.90 (m, 9H).

IR: ν3060, 1694, 1651, 1628, 1492, 1456, 1398, 1278 cm$^{-1}$.

Example 3(6)
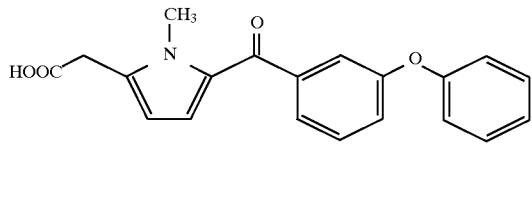
NMR: δ3.75 (s, 2H), 3.94 (s, 3H), 6.12 (d, 1H), 6.69 (d, 1H), 7.00–7.55 (m, 9H).
IR: ν3200, 1730, 1697, 1609, 1575, 1487, 1453, 1375, 1269, 1240, 1197, 1140 cm$^{-1}$
Example 3(7)
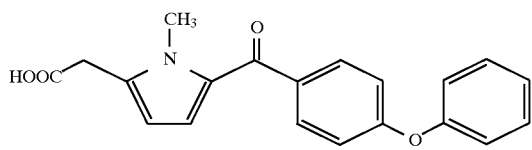
NMR: δ3.77 (s, 2H), 3.94 (s, 3H), 6.14 (d, 1H), 6.69 (d, 1H), 6.95–7.46 (m, 7H), 7.81 (m, 2H).
IR: ν2950, 1720, 1593, 1561, 1485, 1448, 1376, 1238, 1179 cm$^{-1}$.
Example 3(8)
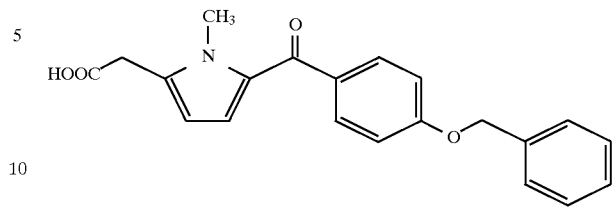
NMR: δ3.77 (s, 2H), 3.94 (s, 3H), 5.14 (s, 2H), 6.13 (d, 1H), 6.68 (d, 1H), 7.04 (d, 2H), 7.43 (m, 5H), 7.83 (d, 2H).
IR: ν3065–2915, 1697, 1656, 1622, 1262, 888, 760 cm$^{-1}$.
Example 3(9)
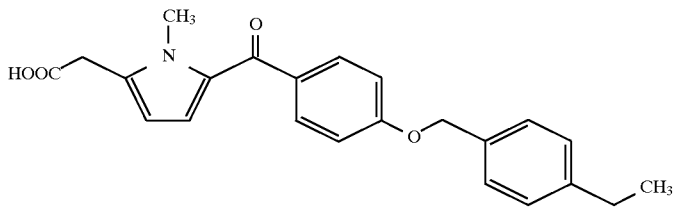
NMR (DMSO-d$_6$): δ7.72 (2H, d), 7.38 (2H, d), 7.24 (2H, d), 7.11 (2H, d), 6.56 (1H, d), 6.09 (1H, d), 5.15 (2H, s), 3.80 (3H, s), 3.76 (2H, s), 2.61 (2H, q), 1.18 (3H, t).
IR: ν3015, 2870, 1695, 1622, 1601, 1482, 1458, 1380, 1271, 1241 cm$^{-1}$.
Example 3(10)
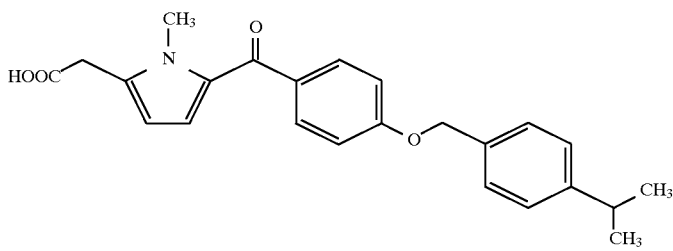
NMR: δ7.82 (2H, d), 7.37 (2H, d), 7.27 (2H, d), 7.02 (2H, d), 6.67 (1H, d), 6.13 (1H, d), 5.09 (2H, s), 3.93 (3H, s), 3.79 (2H, s), 2.93 (1H, m), 1.26 (6H, d).
IR: ν3425, 2960, 1697, 1622, 1601, 1481, 1456, 1379, 1270, 1243, 880, 759 cm$^{-1}$.

Example 3(11)
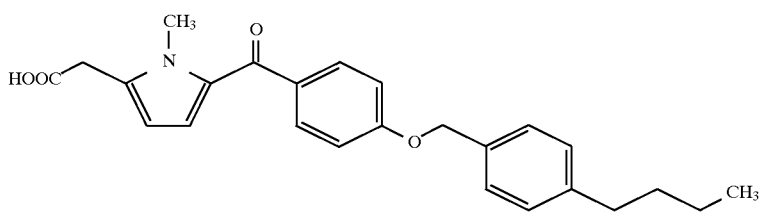
NMR (DMSO-d$_6$): δ7.73 (2H, d), 7.37 (2H, d), 7.23 (2H, d), 7.12 (2H, d), 6.57 (1H, d), 6.11 (1H, d), 5.15 (2H, s), 3.80 (3H, s), 3.78 (3H, s), 2.59 (2H, t), 1.56 (2H, m), 1.32 (2H, m), 0.90 (3H, t).
IR: ν3015, 2855, 1695, 1622, 1601, 1482, 1458, 1396, 1272, 1241 cm$^{-1}$.
Example 3(12)
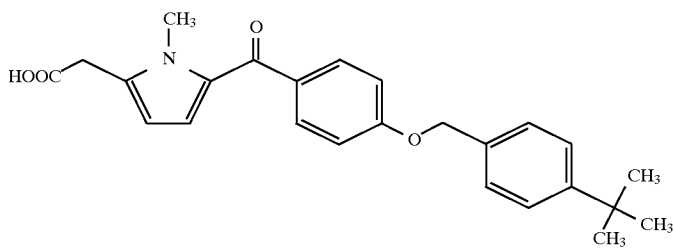
NMR: δ7.83 (2H, d), 7.41 (4H, m), 7.01 (2H, d), 6.68 (1H, d), 6.15 (1H, d), 5.10 (2H, s), 3.94 (3H, s), 3.77 (2H, s), 1.38 (9H, s).
IR: ν2965, 1710, 1617, 1478, 1454, 1376, 1302, 1267, 1243, 1152, 1015, 886, 818, 756 cm$^{-1}$.
Example 3(13)
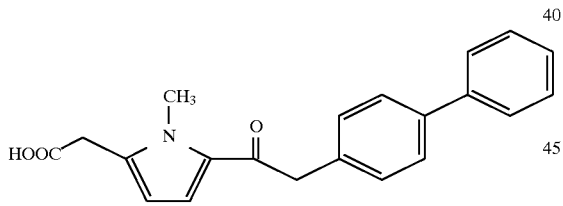
NMR: δ3.71 (s, 2H), 3.87 (s, 3H), 4.10 (s, 2H), 6.15 (d, 1H,), 7.11 (d, 1H), 7.27–7.63 (m, 9H).
IR: ν3030, 1734, 1559, 1487, 1450, 1375, 1186, 1154 cm$^{-1}$.
Example 3(14)
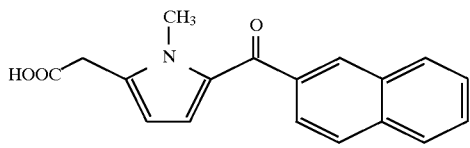
NMR: δ3.81 (s, 2H), 4.01 (s, 3H), 6.18 (d, 1H), 6.76 (d, 1H), 7.56 (m, 2H), 7.91 (m, 4H), 8.32 (s, 1H).
IR: ν3050, 2950, 1696, 1619, 1484, 1457, 1378, 1279, 1238, 770, 738 cm$^{-1}$.
Example 3(15)
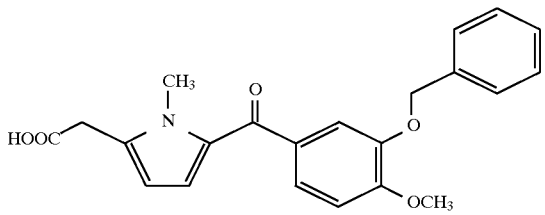
NMR: δ3.75 (s, 2H), 3.91 (s, 3H), 3.95 (s, 3H), 5.19 (s, 2H), 6.08 (d, 1H), 6.50 (d, 1H), 6.92 (m, 1H), 7.26–7.52 (m, 7H).
Example 3(16)
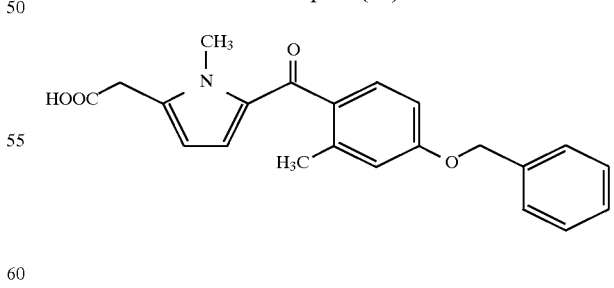
NMR: δ7.55–7.20 (6H, m),6.87–6.74 (2H, m), 6.47 (1H, d,), 6.09 (1H, d), 5.10 (2H, s), 3.99 (3H, s), 3.76 (3H, s), 2.38 (3H, s).
IR: ν3035, 2920, 1711, 1616, 1570, 1497, 1452, 1421, 1397, 1377, 1311, 1263, 1235, 1192, 1102, 993, 870, 847, 752 cm$^{-1}$.

Example 3(17)
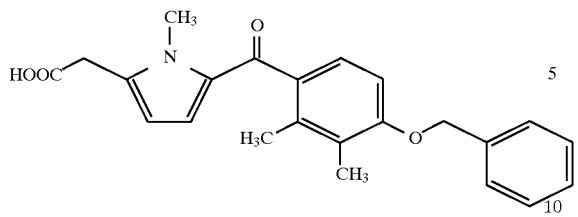
NMR: δ7.50–7.30 (5H, m),7.20 (2H, d), 6.75 (2H, d), 6.46 (1H, d), 6.07 (1H, d), 5.11 (2H, s), 4.01 (3H, s), 3.75 (3H, s), 2.27 (3H, s), 2.25 (3H, s).
IR: ν3030, 1721, 1630, 1592, 1480, 1455, 1370, 1261, 1238, 1217, 1187, 1067, 795, 761, 736 cm$^{-1}$.
Example 3(18)
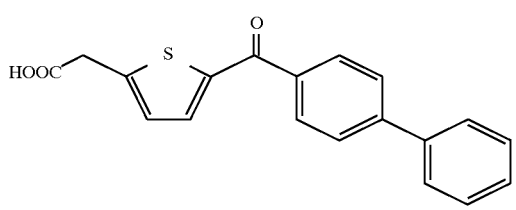
NMR: δ3.97 (s, 2H), 7.07 (d, 1H), 7.38–7.56 (m, 3H), 7.57–7.79 (m, 5H), 7.90–8.02 (m, 2H).
IR: ν3060, 2920, 1696, 1619, 1450, 1405, 1315, 1222 cm$^{-1}$.
Example 3(19)
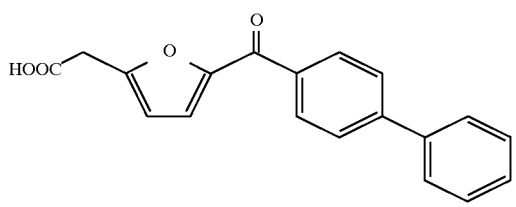
NMR (CDCl$_3$/DMSO-d$_6$ (2 drops)): δ3.83 (s, 2H), 6.65 (d, 1H), 7.23 (d, 1H), 7.30–8.09 (m, 9H).
Example 3(20)
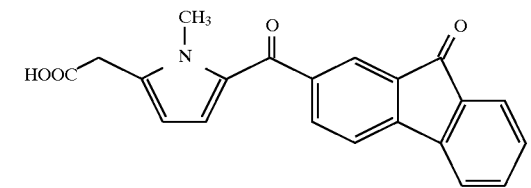
NMR: δ3.78 (s, 2H), 3.98 (s, 3H), 6.17(d, 1H), 6.71 (d, 1H), 7.35–7.41 (m, 1H), 7.52–7.76 (m, 4H), 7.93–8.07 (m, 2H).
IR: ν1716, 1640, 1490, 1456, 1379, 1199, 1100, 746 cm$^{-1}$.
Example 3(21)
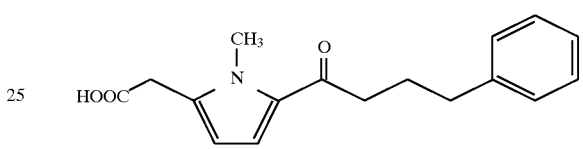
NMR: δ1.95–2.13 (m, 2H), 2.64–2.81 (m, 4H), 3.70 (s, 2H), 3.88 (s, 3H), 6.09 (d, 1H), 6.86 (d, 1H), 7.19–7.28 (m, 5H).
IR: ν2945, 1704, 1640, 1485, 1456, 1421, 1380, 1256, 990, 917, 701 cm$^{-1}$.
Example 3(22)
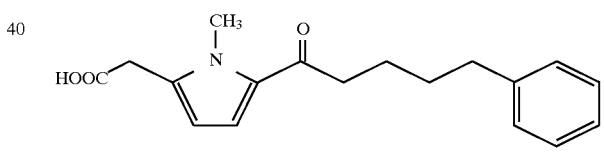
NMR: δ1.70 (m, 4H), 2.64 (t, 2H), 2.77 (t, 2H), 3.70 (s, 2H), 3.87 (s, 3H), 6.10 (d, 1H), 6.92 (d, 1H), 7.10–7.33 (m, 5H).
IR: ν2600–4000, 1693, 1646, 1458, 1258, 1259, 752, 696 cm$^{-1}$.
Example 3(23)
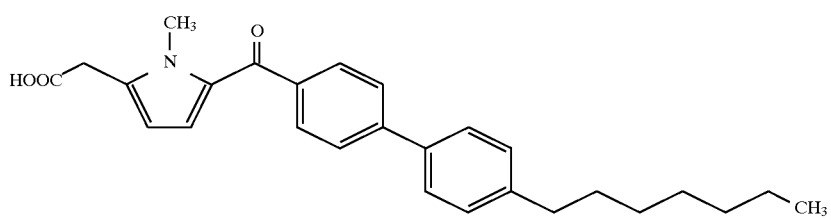

NMR: δ0.89 (t, 3H), 1.32 (m, 8H), 1.68 (m, 2H), 2.65 (t, 2H), 3.79 (s, 2H), 3.98 (s, 3H), 6.17 (d, 1H), 6.75 (d, 1H), 7.26 (d, 2H), 7.57 (d, 2H), 7.65 (d, 2H), 7.85 (d, 2H),

IR: ν3000–3900, 2925, 1695, 1627, 1482, 1458, 1269, 1241 cm$^{-1}$.

Example 3(24)

NMR: δ3.95 (s, 2H), 7.00–7.50 (m, 8H), 7.52 (d, 1H,), 7.87 (d, 2H).

IR: ν3030, 1692, 1619, 1591, 1490, 1456, 1311, 1264, 1166 cm$^{-1}$

Example 3(25)

NMR (CDCl$_3$/DMSO-d$_6$): δ3.63 (s, 2H), 3.66 (s, 3H), 6.62 (d, 1H), 7.22 (d, 1H), 7.30–7.54 (m, 3H), 7.60–7.76 (m, 4H), 7.85–7.96 (m, 2H).

IR: ν3055, 1717, 1610, 1590, 1518, 1430, 1353, 1251, 1199 cm$^{-1}$.

Example 3(26)

NMR (DMSO-d$_6$): δ7.90–7.70 (6H, m), 7.64 (1H, d), 7.56–7.40 (3H, m), 6.89 (1H, d), 6.74 (1H, d), 6.51 (1H, d), 4.03 (3H, s).

IR: ν3030, 1680, 1615, 1516, 1469, 1446, 1376, 1312, 1255, 1211, 960, 888, 745 cm$^{-1}$.

Example 3(27)

NMR: δ7.86 (2H, d), 7.70–7.30 (7H, m), 6.72 (1H, d), 6.01 (1H, d), 3.98 (3H, s), 3.00 (2H, m), 2.79 (2H, m).

IR: ν3425, 3030, 1697, 1615, 1481, 1451, 1406, 1374, 1263, 1224, 1152, 887, 746, 695 cm$^{-1}$.

Example 3(28)

NMR: δ7.85 (2H, d), 7.65 (4H, m), 7.50–7.40 (3H, m), 6.73 (1H), 6.01 (1H, d), 3.96 (3H, s), 2.73 (2H, t), 2.50 (2H, t), 2.04 (2H, m).

IR: ν3030, 1708, 1620, 1478, 1437, 1426, 1399, 1372, 1291, 1258, 1157, 1047, 891, 760 cm$^{-1}$.

Example 3(29)

NMR: δ7.88 (2H, d), 7.65 (4H, m), 7.55–7.40 (3H, m), 7.40–7.15 (3H, m), 7.02 (2H, d), 6.85 (1H, d), 6.27 (1H, d), 5.80 (2H, s), 3.65 (2H, s).

IR: ν3060, 1717, 1618, 1537, 1478, 1452, 1424, 1390, 1269, 1204, 1152, 1053, 882, 848, 746 cm$^{-1}$.

Example 3(30)

NMR: δ7.87 (2H, d), 7.65 (4H, m), 7.50–7.35 (3H, m), 6.73 (1H, d), 6.01 (1H, d), 3.96 (3H, s), 2.68 (2H, t), 2.45 (2H, t,), 1.78 (4H, m).

IR: ν3025, 2875, 1699, 1610, 1479, 1456, 1432, 1406, 1374, 1314, 1257, 1207, 1174, 1035, 1005, 961, 938, 881, 852, 786, 751, 728, 700 cm$^{-1}$.

Example 3(31)
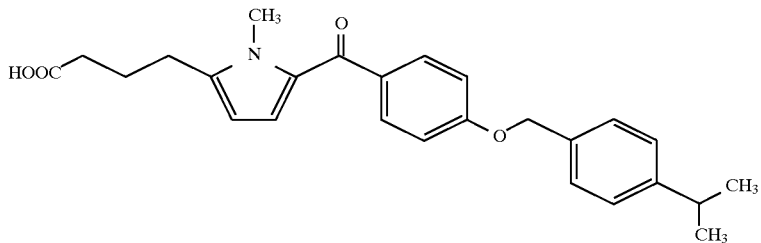
NMR: δ7.80 (2H, d), 7.37 (2H, d), 7.26 (2H, d), 7.01 (2H, d), 6.66 (1H, d), 5.98 (1H, d), 5.09 (2H, s), 3.92 (3H, s), 2.93 (1H, m), 2.72 (2H, t), 2.50 (2H, t), 2.03 (2H, m), 1.26 (6H, d).
IR: ν3035, 2890, 1707, 1619, 1480, 1458, 1422, 1375, 1308, 1260, 1172, 1046, 891, 751 cm$^{-1}$.
Example 3(32)
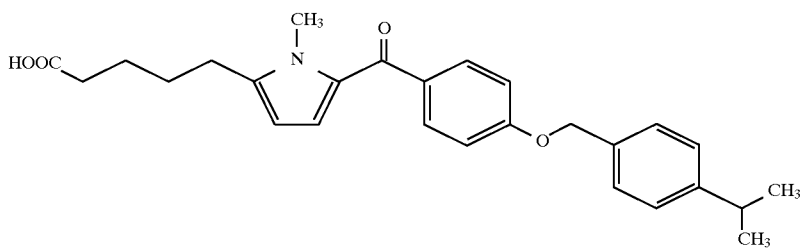
NMR: δ7.80 (2H, d), 7.37 (2H, d), 7.26 (2H, d), 7.01 (2H, d), 6.66 (1H, d), 5.97 (1H, d), 5.09 (2H, s), 3.91 (3H, s), 2.93 (1H, m), 2.66 (2H, t), 2.44 (2H, t), 1.76 (4H, m), 1.26 (6H,d).
IR: ν2966, 1697, 1607, 1479, 1449, 1373, 1314, 1251, 889 cm$^{-1}$.
Example 3(33)
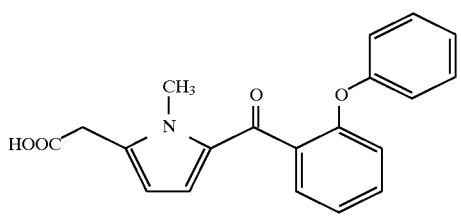
NMR: δ3.71 (s, 2H), 3.85 (s, 3H), 6.09 (d, 1H), 6.61 (d, 2H), 6.88–7.50 (m, 9H).
IR: ν2900–3100, 1708, 1622, 1487, 1454, 1378, 1232, 747 cm$^{-1}$.
Example 3(34)
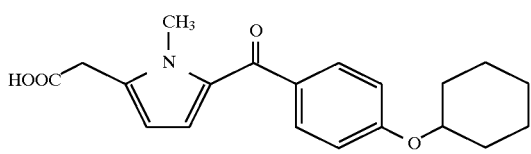
NMR: δ1.20–2.10 (m, 10H), 3.76 (s, 2H), 3.93 (s, 3H), 4.36 (m, 1H), 6.13 (d, 1H), 6.68 (d, 1H), 6.91 (d, 2H), 7.80 (d, 2H).
Example 3(35)
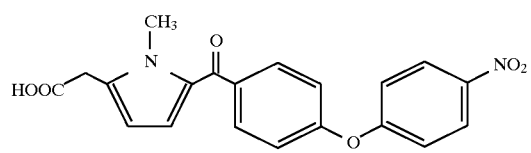
NMR (DMSO-d$_6$): δ3.64 (s, 2H), 3.86 (s, 3H), 6.10 (d, 1H), 6.63 (d, 1H), 7.27 (d, 4H), 7.83 (d, 2H), 8.32 (d, 2H).
IR: ν3080, 2930, 1707, 1619, 1635, 1515, 1486, 1341, 1251, 1165, 887, 751 cm$^{-1}$.
Example 3(36)
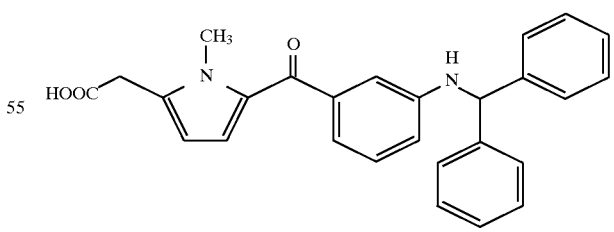
NMR: δ3.74 (s, 2H), 3.92 (s, 3H), 5.55 (s, 1H), 6.03 (d, 1H), 6.45 (d, 1H), 6.70 (m, 1H), 6.97 (s, 1H), 7.08–7.40 (m, 13H).
IR: ν3400–3060, 1729, 1590, 1531, 1487, 1451, 1375, 747, 700 cm$^{-1}$.

Example 3(37)
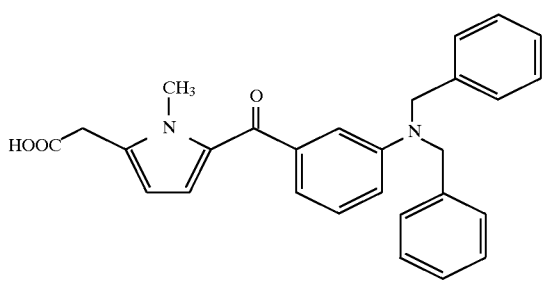
NMR: δ3.70 (s, 2H), 3.89 (s, 3H), 4.68 (s, 4H), 5.98 (d, 1H), 6.46 (d, 1H), 6.89 (bd, 1H), 7.08–7.36 (m, 13H).
IR: ν3200–2900, 1745, 1717, 1595, 1569, 1492, 1451, 1364, 1261, 749, 739, 697 cm$^{-1}$.
Example 3(38)
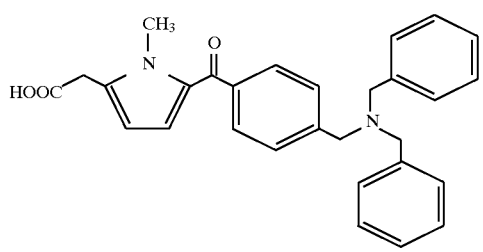
NMR: δ3.59 (s, 4H), 3.62 (s, 2H), 3.74 (s, 2H), 3.94 (s, 3H), 6.11 (d, 1H), 6.66 (d, 1H), 7.20–7.55 (m, 12H), 7.74 (d, 2H).
IR: ν3060, 1730, 1619, 1558, 1403, 1452, 1374 cm$^{-1}$.
Example 3(39)
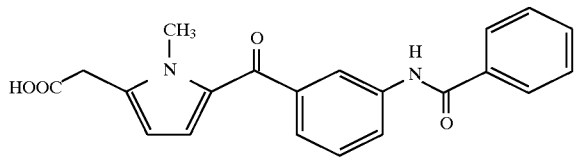
NMR (DMSO-d$_6$): δ3.80 (s, 2H), 3.85 (s, 3H), 6.14 (d, 1H), 6.68 (s, 1H), 7.42–7.66 (m, 5H), 7.99 (m, 3H), 8.20 (s, 1H), 10.43 (s, 1H).
IR: ν3200–2955, 1733, 1675, 1578, 1549, 1473, 1376, 1262, 1201, 748 cm$^{-1}$.
Example 3(40)
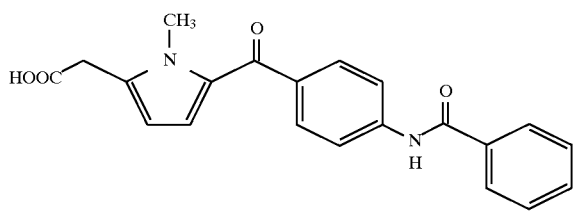
NMR (DMSO-d$_6$): δ3.80 (s, 2H), 3.83 (s, 3H), 6.14 (d, 1H), 6.62 (d, 1H), 7.58 (m, 3H), 7.77 (m, 2H), 8.00 (m, 4H), 10.53 (s, 1H).
IR: ν3500–2800, 1731, 1653, 1596, 1518, 1488, 1263, 758, 708 cm$^{-1}$.
Example 3(41)
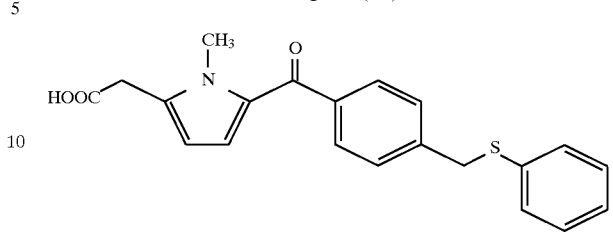
NMR: δ3.76 (s, 2H), 3.95 (s, 3H), 4.14 (s, 2H), 6.13 (d, 1H), 6.65 (d, 1H), 7.17–7.42 (m, 7H), 7.70 (d, 2H).
IR: ν3060, 1701, 1624, 1482, 1377, 1264, 1232 cm$^{-1}$.
Example 3(42)
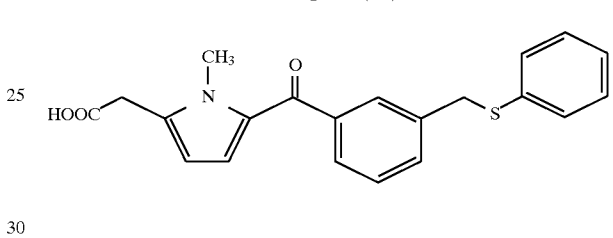
NMR: δ3.78 (s, 2H), 3.96 (s, 3H), 4.14 (s, 2H), 6.13 (d, 1H), 6.51 (d, 1H), 7.19–7.68 (m, 9H).
Example 3(43)
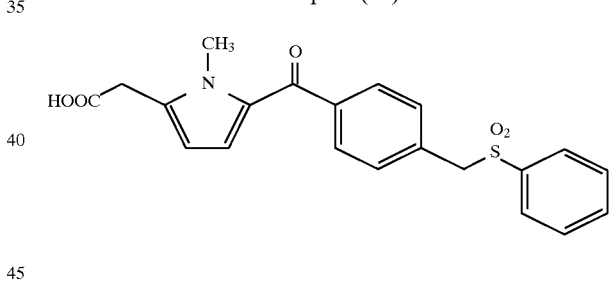
NMR: δ3.70 (s, 2H), 3.98 (s, 3H), 4.11 (s, 2H), 6.14 (d, 1H), 6.62 (d, 1H), 7.04 (d, 2H), 7.42–7.49 (m, 5H), 7.66 (d, 2H).
IR: ν1719, 1626, 1480, 1375, 1261, 1209, 1045, 885, 750 cm$^{-1}$.
Example 3(44)
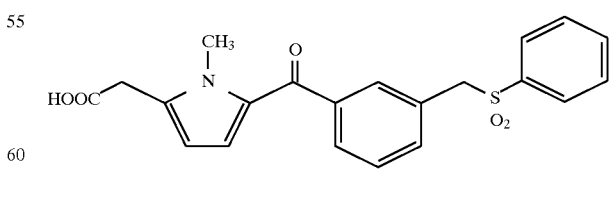
NMR: δ3.77 (s, 2H), 3.94 (s, 3H), 4.10 (s, 2H), 6.12 (d, 1H), 6.53 (d, 1H), 7.13–7.75 (m, 9H).
IR: ν1724, 1618, 1616, 1591, 1489, 1451, 1379, 1273, 1179, 753 cm$^{-1}$.

Example 3(45)
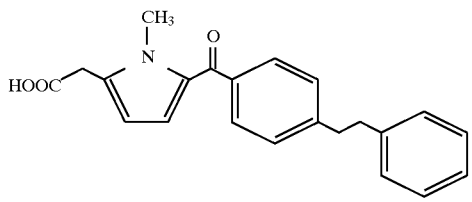
NMR: δ7.72 (2H, d), 7.32–7.15 (7H, m), 6.68 (1H, d), 6.14 (1H, d), 3.97 (3H, s), 3.77 (2H, s), 2.97 (4H, m).
IR: ν3065, 2965, 1716, 1622, 1559, 1487, 1457, 1421, 1376, 1267, 1232, 886 cm$^{-1}$.
Example 3(46)
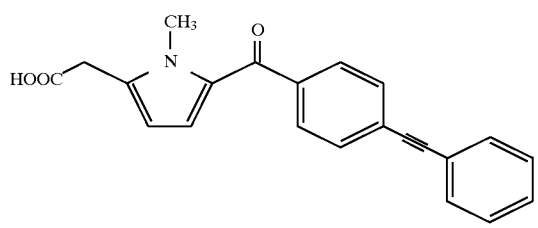
NMR: δ3.70 (2, 2H), 3.87 (s, 3H), 6.15 (d, 1H), 6.68 (d, 1H), 7.37 (m, 3H), 7.54 (m, 2H), 7.57 (d, 2H), 7.78 (d, 2H).
IR: ν3015, 1698, 1620, 1592, 1486, 1456, 1378, 1264 cm$^{-1}$.
Example 3(47)
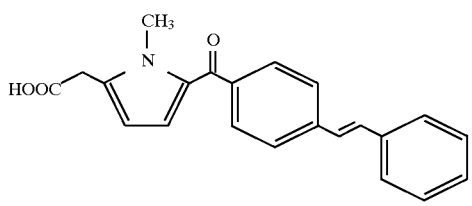
NMR: δ7.75–7.65 (6H, m), 7.46–7.32 (5H, m), 6.64 (1H, d), 6.15 (1H, d), 3.86 (3H, s), 3.82 (2H, s).
IR: ν3030, 1732, 1700, 1570, 1541, 1489, 1457, 1420, 1398, 1268, 1242, 960, 887, 762, 685 cm$^{-1}$.
Example 3(48)
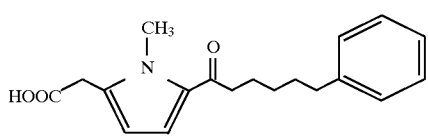
NMR: δ1.35–1.48 (m, 2H), 1.60–1.80 (m, 4H), 2.61 (t, 2H), 2.75 (t, 2H), 3.71 (s, 2H), 3.88 (s, 3H), 6.10 (d, 1H), 6.92 (d, 1H), 7.15–7.30 (m, 5H).
IR: ν2930, 1698, 1635, 1490, 1462, 1420, 1238, 917, 774, 746, 694 cm$^{-1}$.
Example 3(49)
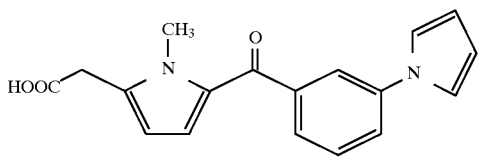
NMR: δ3.79 (s, 2H), 3.99 (s, 3H), 6.16 (d, 1H), 6.36 (t, 2H), 6.72 (d, 1H), 7.13 (t, 2H), 7.43–7.68 (m, 3H), 7.81 (s, 1H).
IR: ν2955, 1743, 1572, 1490, 1380, 1242, 1168, 746 cm$^{-1}$
Example 3(50)
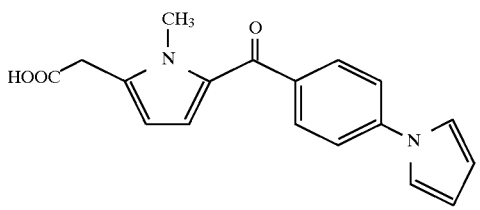
NMR: δ3.78 (s, 2H), 3.98 (s, 3H), 6.19 (d, 1H), 6.40 (m, 2H), 6.73 (d, 1H), 7.17 (m, 2H), 7.48 (d, 2H), 7.92 (d, 2H).
IR: ν3100–2955, 1698, 1646, 1621, 1331, 1267, 884, 758, 717 cm$^{-1}$.
Example 3(51)
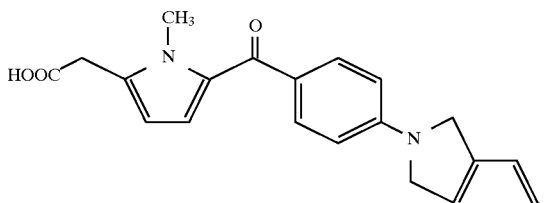
NMR (DMSO-d$_6$): δ3.24 (s, 2H), 3.81 (s, 3H), 4.71 (s, 4H), 5.87 (d, 1H), 6.49 (d, 1H), 6.73 (d, 2H), 7.29–7.43 (m, 4H), 7.73 (d, 2H).
IR: ν3500–2800, 1606, 1471, 1367, 1274, 1181, 1148, 883, 758 cm$^{-1}$.
Example 3(52)
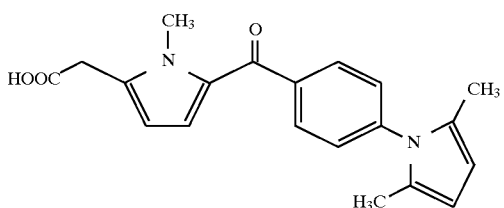
NMR: δ2.07 (s, 6H), 3.80 (s, 2H), 3.99 (s, 3H), 5.93 (s, 2H), 6.18 (d, 1H), 6.76 (d, 1H), 7.28 (d, 2H), 7.90 (d, 2H).
IR: ν3200, 2800, 1718, 1616, 1406, 1263, 1226, 884 cm$^{-1}$

Example 3(53)

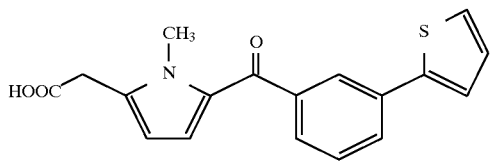

NMR: δ3.78 (s, 2H), 3.99 (s, 3H), 6.15 (d, 1H), 6.73 (d, 1H), 7.07 (m, 1H), 7.25–7.52 (m, 3H), 7.62–7.82 (m, 2H), 8.01 (s, 1H).

IR: ν3105, 1734, 1699, 1623, 1595, 1489, 1454, 1375 cm$^{-1}$.

Example 3(54)

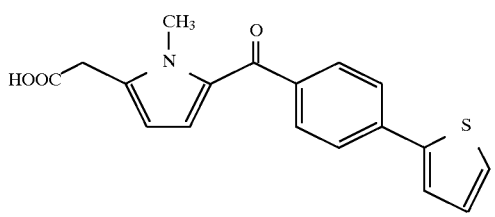

NMR (CDCl$_3$/DMSO-d$_6$): δ3.70 (s, 2H), 3.87 (s, 3H), 6.14 (d, 1H), 6.72 (d, 1H), 7.14 (M, 1H), 7.32–7.48 (m, 2H), 7.68 (m, 2H), 7.83 (m, 2H).

IR: ν2950, 1735, 1699, 1626, 1600, 1483, 1456, 1379, 1259 cm$^{-1}$.

Example 3(55)

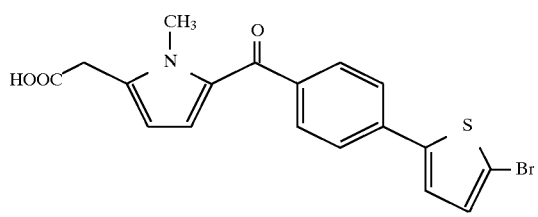

NMR: δ3.70 (s, 2H), 3.97 (s, 3H), 6.15 (d, 1H), 6.70 (d, 1H), 7.06 (d, 1H), 7.15 (d, 1H), 7.57 (d, 2H), 7.81 (d, 2H).

IR: ν1695, 1622, 1484, 1458 1429, 1379, 1268, 979, 758 cm$^{-1}$.

Example 3(56)

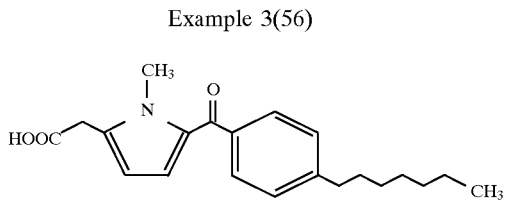

NMR: δ0.82–0.93 (m, 2H), 1.22–1.39 (m, 8H), 1.59–1.75 (m, 2H), 2.66 (t, 3H), 3.77 (s, 2H), 3.96 (s, 3H), 6.14 (d, 1H), 6.69 (d, 1H), 7.24 (d, 2H), 7.72 (d, 2H).

IR: ν1735, 1697, 1622, 1487, 1457, 1378, 1269, 1238, 887 cm$^{-1}$.

Example 3(57)

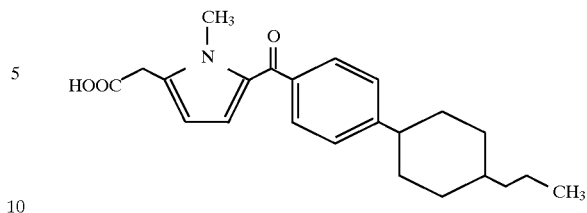

NMR: δ0.91 (t, 3H), 1.00–1.58 (m, 9H), 1.90 (m, 4H), 2.52 (m, 1H), 3.77 (s, 2H), 3.96 (s, 3H), 6.14 (d, 1H), 6.70 (d, 1H), 7.28 (d, 2H), 7.75 (d, 2H).

Example 3(58)

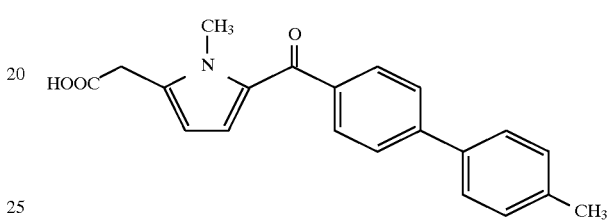

NMR: δ2.41 (s, 3H), 3.79 (s, 2H), 3.98 (s, 3H), 6.16 (d, 1H), 6.75 (d, 1H), 7.27 (d, 2H), 7.54 (d, 2H), 7.65 (d, 2H), 7.86 (d, 2H).

IR: ν1730, 1617, 1588, 1486, 1451, 1400, 1379, 1264, 1199, 877, 814, 761 cm$^{-1}$.

Example 3(59)

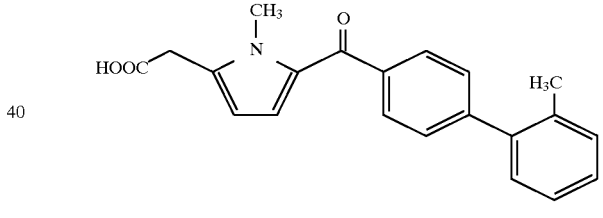

NMR: δ2.29 (s, 3H), 3.79 (s, 2H), 3.99 (s, 3H), 6.17 (d, 1H), 6.78 (d, 1H), 7.28 (m, 4H), 7.40 (d, 2H), 7.85 (d, 2H).

IR: ν3020, 1731, 1700, 1618, 1481, 1453, 1406, 1376, 1262 cm$^{-1}$.

Example 3(60)

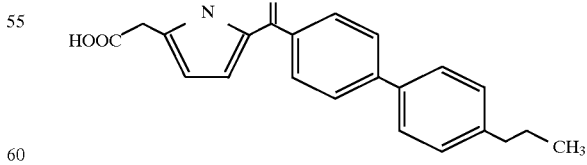

NMR: δ0.98 (t, 3H), 1.67 (q, 2H), 2.64 (t, 2H), 3.79 (s, 2H), 3.99 (s, 3H), 6.19 (d, 1H), 6.75 (d, 1H), 7.28 (d, 2H), 7.54–7.68 (m, 4H), 7.87 (d, 2H).

IR: ν2955, 1698, 1672, 1601, 1401, 1457, 1398, 1267, 761 cm$^{-1}$.

Example 3(61)
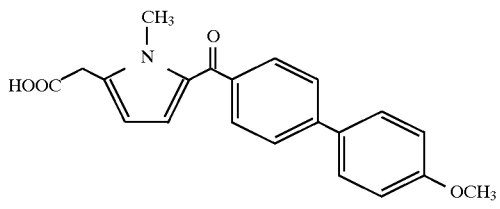
NMR (DMSO-d$_6$): δ3.83 (s, 5H), 3.86 (s, 3H), 6.16 (d, 1H), 6.66 (d, 1H), 7.08 (d, 2H), 7.72 (d, 2H), 7.78 (m, 4H).
IR: ν3035, 2910, 1733, 1695, 1627, 1600, 1525, 1483, 1458, 1378, 1295, 1268 cm$^{-1}$.
Example 3(62)
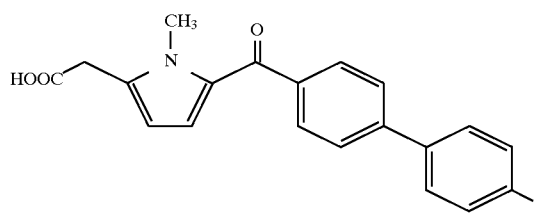
NMR: δ3.79 (s, 2H), 3.98 (s, 3H), 6.17 (d, 1H), 6.74 (d, 1H), 7.15 (m, 2H), 7.63 (m, 4H), 7.89 (m, 2H).
IR: ν3020, 1732, 1698, 1624, 1484, 1456, 1378, 1266 cm$^{-1}$.
Example 3(63)
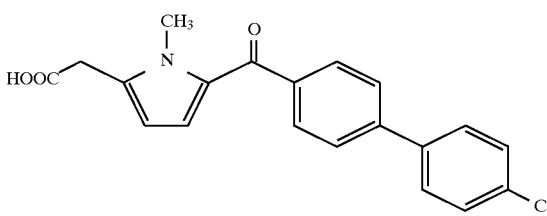
NMR (DMSO-d$_6$): δ3.75 (s, 2H), 3.86 (s, 3H), 6.12 (d, 1H), 6.63 (d, 1H), 7.56 (d, 4H), 7.77 (d, 4H).
IR: ν3035, 1713, 1621, 1633, 1480, 1453, 1376, 1265, 885, 822, 760 cm$^{-1}$.
Example 3(64)
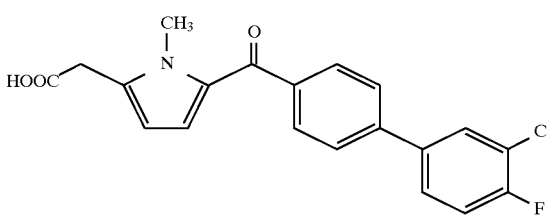
NMR: δ3.79 (s, 2H), 3.99 (s, 3H), 6.17 (d, 1H), 6.73 (d, 1H), 7.23 (m, 1H), 7.47 (m, 1H), 7.60 (d, 2H), 7.65 (m, 1H), 7.87 (d, 2H).
IR: ν3020, 1732, 1701, 1621, 1484, 1455, 1379, 1266 cm$^{-1}$.
Example 3(65)
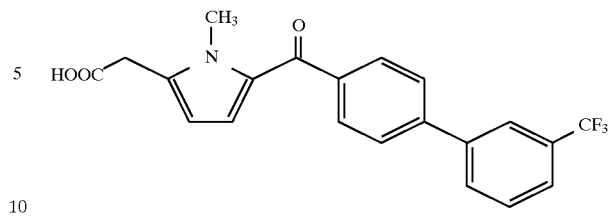
NMR: δ3.80 (s, 2H), 4.00 (s, 3H), 6.18 (d, 1H), 6.74 (d, 1H), 7.53–7.96 (m, 8H).
IR: ν3030, 1731, 1690, 1625, 1483, 1455, 1378, 1333, 1259, 1179, 1123 cm$^{-1}$.
Example 3(66)
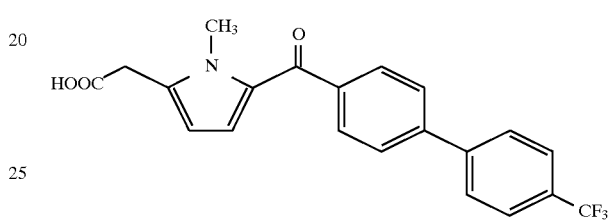
NMR (DMSO-d$_6$): δ3.82 (s, 2H), 3.87 (s, 3H), 6.14–6.16 (d, 1H), 6.65–6.67 (d, 1H), 7.86–8.01 (m, 8H).
IR: ν3050, 1713, 1620, 1486, 1454, 1397, 1376, 1325, 1265, 1168, 1124, 1072, 885, 832, 764, 737 cm$^{-1}$.
Example 3(67)
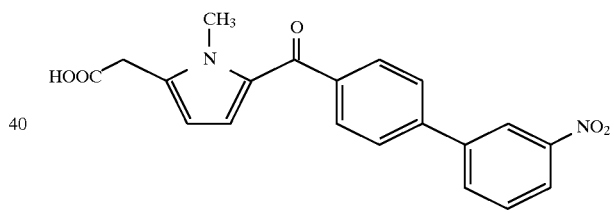
NMR (DMSO-d$_6$): δ8.53 (1H, d), 8.26 (2H, m), 7.96–7.80 (5H, m), 6.66 (1H, d), 6.15 (1H, d), 3.87 (3H, s), 3.82 (2H, s).
IR: ν3100, 2995, 1732, 1619, 1530, 1455, 1377, 1348, 1264, 886, 771, 735 cm$^{-1}$.
Example 3(68)
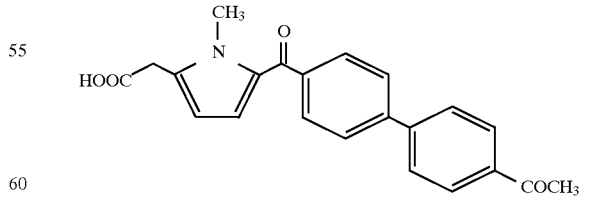
NMR (DMSO-d$_6$): δ2.63 (s, 3H), 3.79 (s, 2H), 3.86 (s, 3H), 6.14 (d, 1H), 6.65 (d, 1H), 7.75–7.94 (m, 6H), 8.10 (d, 2H).
IR: ν3395, 2925, 1763, 1700, 1619, 1455, 1376, 1264, 885, 762 cm$^{-1}$.

Example 3(69)
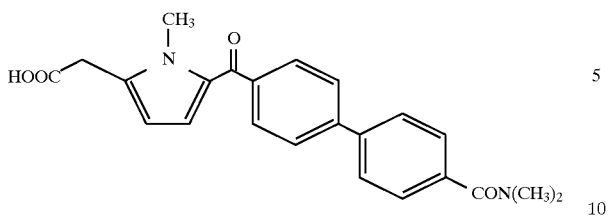
NMR: δ7.85 (2H, d), 7.64 (4H, m), 7.51 (2H, d), 6.65 (1H, d), 6.09 (1H, d), 3.97 (3H, s), 3.73 (2H, s), 3.12 (3H, broad s), 3.05 (3H, broad s).
IR: ν3445, 3030, 1731, 1699, 1622, 1567, 1539, 1504, 1480, 1452, 1398, 1377, 1264, 885, 837, 752 cm$^{-1}$.
Example 3(70)
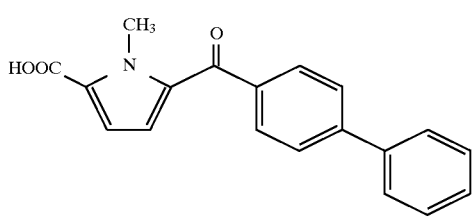
NMR: δ7.94 (2H, d), 7.74–7.64 (4H, m), 7.53–7.43 (3H, m), 7.08 (1H, d), 6.70 (1H, d), 4.30 (3H, s).
IR: ν3060, 1702, 1653, 1630, 1601, 1507, 1447, 1372, 1258, 887, 745 cm$^{-1}$.
Example 3(71)
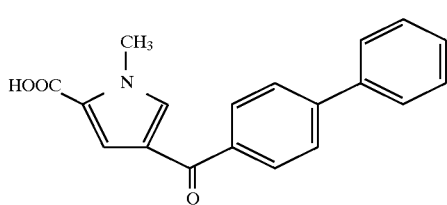
NMR (DMSO-d$_6$): δ7.90–7.73 (7H, m), 7.56–7.43 (3H, m), 7.21 (1H, d), 3.94 (3H, s).
IR: ν3113, 2960, 1678, 1629, 1601, 1535, 1496, 1467, 1400, 1373, 1288, 1249, 1206, 1134, 1104, 1077, 886, 749 cm$^{-1}$.
Example 3(72)
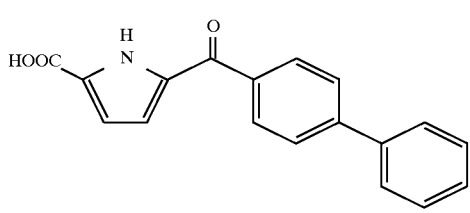
NMR (DMSO-d$_6$): δ7.96 (2H, d), 7.87 (2H, m), 7.79 (2H, d), 7.58–7.45 (3H, m), 6.86 (2H, m).
IR: ν3265, 1691, 1602, 1406, 1273, 1211, 887, 743 cm$^{-1}$.
Example 3(73)
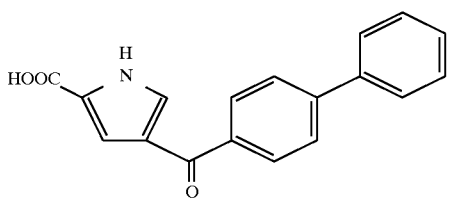
NMR (DMSO-d$_6$): δ7.93–7.75 (6H, m), 7.57–7.40 (4H, m), 7.12 (1H, s).
IR: ν3330, 1697, 1673, 1620, 1447, 1387, 1280, 1235, 1194, 1123, 885, 746 cm$^{-1}$.
Example 3(74)
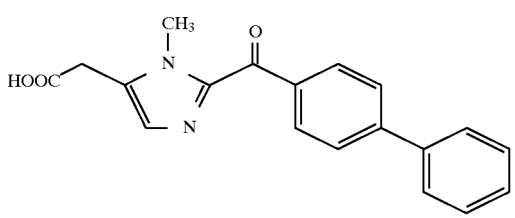
NMR: δ9.95 (1H, br.), 8.18 (2H, d), 7.71–7.61 (4H, m), 7.50–7.37 (3H, m), 7.19 (1H, s), 3.87 (3H, s), 3.64 (2H, s).
IR: ν3030, 1730, 1703, 1648, 1600, 1472, 1432, 1375, 1267, 1226, 1195, 1160, 905, 752 cm$^{-1}$.
Example 3(75)
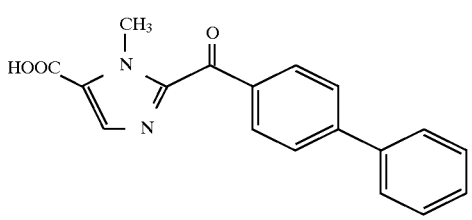
NMR (CDCl$_3$+2 drops of DMSO-d$_6$): δ8.28 (2H, d), 7.87 (1H, s), 7.72 (2H, d), 7.65 (2H, m), 7.52–7.40 (3H, m), 4.31 (3H, s).
IR: ν3135, 2965, 1707, 1652, 1600, 1518, 1407, 1259, 1195, 907, 752 cm$^{-1}$.
Example 3(76)
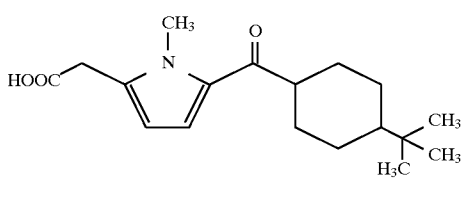
NMR: δ0.87 (s, 9H), 0.95–2.00 (m, 9H), 2.85–3.05 (m, 1H), 3.71 (s, 2H), 3.88 (s, 3H), 6.10–6.12 (d, 1H), 6.96–6.98 (d, 1H).
IR: ν2945, 1700, 1646, 1486, 1461, 1417, 1384, 1296, 1254, 989, 918, 818, 765 cm$^{-1}$.

Example 3(77)

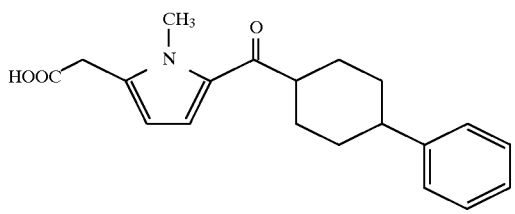

NMR: δ1.40–2.10 (m, 8H), 2.50–2.75 (m, 1H), 3.00–3.32 (m, 1H), 3.72 (two s, 2H), 3.87 (two s, 3H), 6.12 (two d, 1H), 7.00 (two d, 1H), 7.13–7.37 (m, 5H).

IR: ν3060, 2930, 1733, 1638, 1489, 1453, 1305, 1248 cm$^{-1}$

Example 3(78)

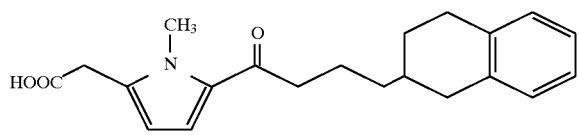

NMR: δ1.72–2.08 (m,6H), 2.56–2.81 (m,9H), 3.70 (s,2H), 3.88 (s,3H), 6.09 (d,1H), 6.88–7.00 (m,5H).

IR: ν2075, 1722, 1596, 1495, 1457, 1407, 1383, 1303, 1202, 1121, 1048, 930, 771, 740, 669 cm$^{-1}$.

Example 3(79)

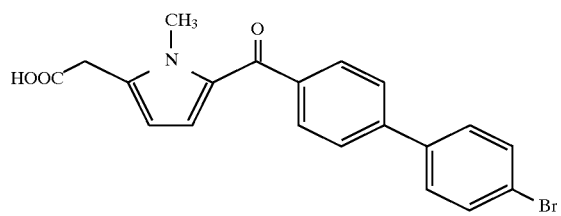

NMR (DMSO-d$_6$): δ3.80 (s, 2H), 3.86 (s, 3H), 6.13 (d, 1H), 6.64 (d, 1H), 7.71 (s, 4H), 7.81 (s, 4H).

IR: ν3030, 1731, 1701, 1620, 1475, 1452, 1374, 1261, 882, 817, 757 cm$^{-1}$.

Example 3(80)

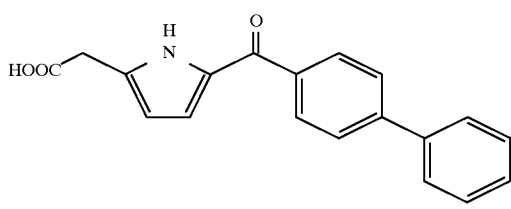

NMR (CDCl$_3$+2 drops of DMSO-d$_6$): δ11.44 (1H, broad), 7.92 (2H, d), 7.66 (4H, m), 7.52–7.38 (3H, m), 6.80 (1H, dd), 6.17 (1H, dd), 3.73 (2H, s).

IR: ν3275, 1713, 1593, 1494, 1425, 1275, 1238, 884, 777, 748 cm$^{-1}$.

Example 3(81)

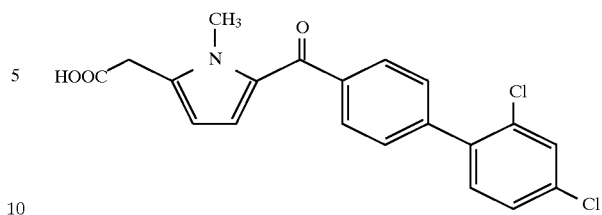

NMR (DMSO-d$_6$): δ3.56 (s, 2H), 3.88 (s, 3H), 6.05 (d, 1H), 6.61 (d, 1H), 7.50–7.63 (m, 4H), 7.73–7.85 (m, 3H)

IR: ν3505, 1713, 1619, 1589, 1483, 1453, 1371, 1261 cm$^{-1}$

Example 3(82)

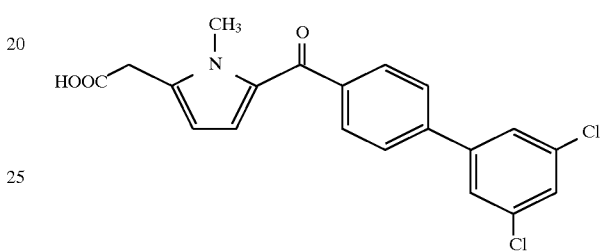

NMR (DMSO-d$_6$): δ3.63 (s, 2H), 3.89 (s, 3H), 6.08 (d, 1H), 6.61 (d, 1H), 7.65–7.95 (m, 7H).

IR: ν3445, 3065, 2950, 1714, 1618, 1585, 1481, 1451, 1371, 1260 cm$^{-1}$

Example 3(83)

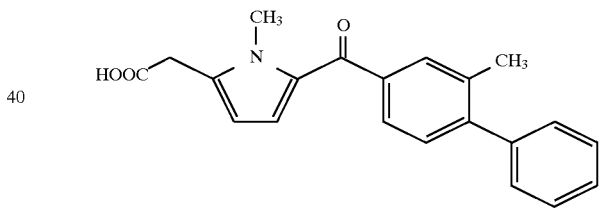

NMR: δ2.32 (s, 3H), 3.79 (s, 2H), 3.98 (s, 3H), 6.17 (d, 1H), 6.77 (d, 1H), 7.25–7.50 (m, 6H), 7.62–7.75 (m, 2H).

IR: ν2950, 1725, 1586, 1484, 1448, 1396, 1370, 1253, 1175 cm$^{-1}$

Example 3(84)

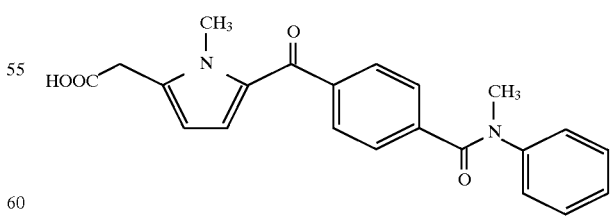

NMR: δ3.52 (s, 3H), 3.72 (s, 2H), 3.90 (s, 3H), 6.07 (d, 1H), 6.51 (d, 1H), 7.05 (m, 2H), 7.18 (m, 3H), 7.34 (d, 2H), 7.55 (d, 2H).

IR: ν3055, 1730, 1618, 1587, 1489, 1372, 1295, 1275 cm$^{-1}$.

Example 3(85)

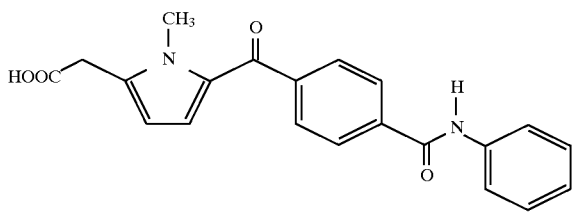

NMR (DMSO$_{d6}$): δ3.83 (s, 2H), 3.89 (s, 3H) 6.17 (d, 1H), 6.62 (d, 1H), 7.13 (m, 1H), 7.38 (m, 2H), 7.82 (m, 4H), 8.07 (m, 2H), 10.41 (s, 1H).

IR: ν3340, 3055, 1714, 1664, 1598, 1534, 1486, 1440, 1373, 1322, 1258 cm$^{-1}$.

Example 3(86)

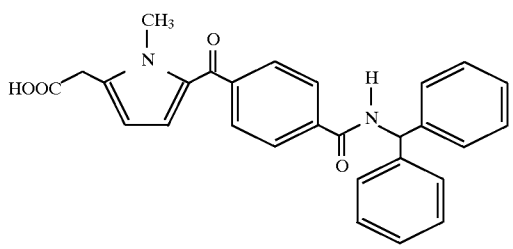

NMR (DMSO$_{d6}$): δ3.89 (s, 5H), 6.01 (d, 1H), 6.45 (d, 1H), 6.54 (d, 1H), 7.35 (m, 10H), 7.72–8.10 (m, 4H), 9.43 (d, 1H).

IR: ν3420, 1623, 1524, 1486, 1450, 1367, 1271, 1186 cm$^{-1}$.

Example 3(87)

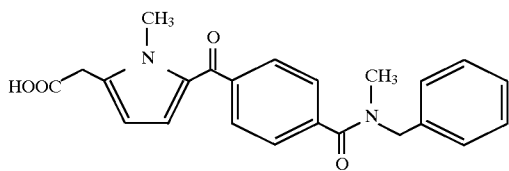

NMR (DMSO$_{d6}$): δ2.87 and 2.92 (singles, total 3H), 3.82 (s, 2H), 3.86 (s, 3H), 4.51 and 4.72 (singles, total, 2H), 6.14 (d, 1H), 6.63 (d, 1H), 7.16–7.87 (m, 9H).

IR: ν3025, 1722, 1619, 1597, 1488, 1450, 1402, 1375, 1258, 1199 cm$^{-1}$.

Example 3(88)

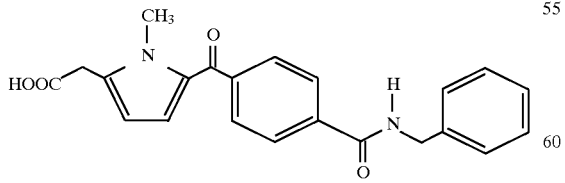

NMR: δ3.76 (s, 2H), 3.98 (s, 3H), 4.67 (d, 2H), 6.14 (d, 1H), 6.52 (t, 1H), 6.63 (d, 1H), 7.36 (m, 4H), 7.82 (m, 5H).

IR: ν3270, 3055, 1718, 1616, 1539, 1484, 1450, 1373, 1258, 1201 cm$^{-1}$.

Example 3(89)

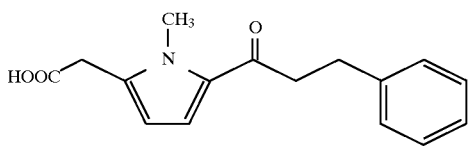

NMR: δ3.06 (m, 4H), 3.71 (s, 2H), 3.89 (s, 3H), 6.10 (d, 1H), 6.93 (d, 1H), 7.25 (m, 5H).

IR: ν3025, 2900, 1690, 1644, 1481, 1455, 1345, 1223, 969, 759 cm$^{-1}$.

Example 3(90)

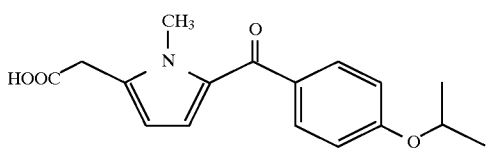

mp 152°–155° C.

NMR: δ1.37 (d, 6H), 3.77 (s, 2H), 3.93 (s, 3H), 4.64 (m, 1H), 6.14 (d, 1H), 6.68 (d, 1H), 6.90 (d, 2H), 7.80 (d, 2H).

IR: ν2960, 1725, 1602, 1557, 1487, 1455, 1380, 1297, 1196, 1150, 1047, 888, 837, 756 cm$^{-1}$

Example 3(91)

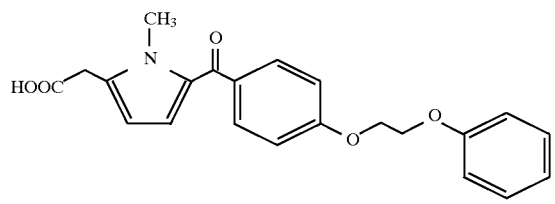

mp 180°–185° C.

NMR: δ3.77 (s, 2H), 3.94 (s, 3H), 4.36–4.38 (m, 4H), 6.14 (d, 1H), 6.67 (d, 1H), 6.94–7.01 (m, 5H), 7.26–7.37 (m, 2H), 7.83 (d, 2H).

IR: ν2955, 1695, 1624, 1599, 1496, 1455, 1328, 1299, 1272, 1240, 1174, 945, 844, 784, 678 cm$^{-1}$.

Example 3(92)

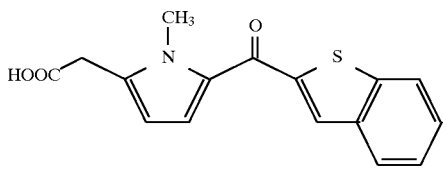

mp 174°–178° C.

NMR: δ3.80 (s, 2H), 3.94 (s, 3H), 6.22 (d, 1H), 7.08 (d, 1H), 7.43 (m, 2H), 7.87 (m, 2H), 7.96 (s, 1H).

IR: ν3039, 2955, 1697, 1609, 1511, 1451, 1374, 1262, 1180, 749 cm$^{-1}$

Example 3(93)

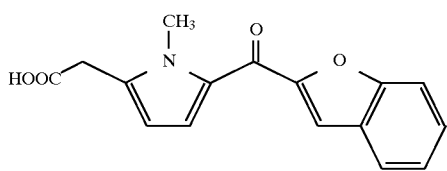

mp 182°–183° C.

NMR: δ3.80 (s, 2H), 3.97 (s, 3H), 6.24 (d, 1H), 7.26–7.73 (m, 6H).

IR: ν3065, 2960, 1692, 1600, 1542, 1451, 1373, 1224, 1194, 1136, 850, 746 cm$^{-1}$.

Formulation example

The following components were admixed in conventional method and punched out to obtain 100 tablets each containing 50 mg of active ingredient.

| | |
|---|---|
| 2-[5-(4-phenylbenzoyl)-1-methylpyrrol-2-yl] acetic acid | 5 g |
| Cellulose calcium gluconate (disintegrating agent) | 0.2 g |
| Magnesium stearate (lubricating agent) | 0.1 g |
| Microcrystalline cellulose | 4.7 g |

What is claimed is:

1. A pharmaceutical composition for the treatment of diseases induced by the excess generation of dihydrotestosterone in mammals, alopecia, acnes, hypertrophy of prostate and prostatic cancer, which comprises, as active ingredient, and effective amount of a compound of the formula (1a):

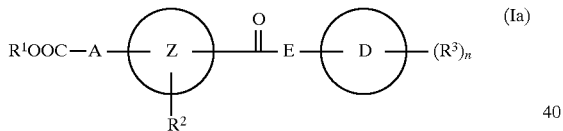 (Ia)

wherein

Ⓩ is pyrrole included nitrogen substituted by $R^4$, thiophene, furan, imidazole included nitrogen substituted by $R^4$, thiazole, oxazole, triazole included nitrogen substituted by $R^4$, in which $R^4$ is hydrogen, C1–4 alkyl, phenyl or phenyl(C1–4)alkyl;

A is bond, C1–6 alkylene or C2–6 alkenylene;

E is bond or C1–6 alkylene;

Ⓓ is benzene, C4–7 cycloalkane, naphthalene, benzo(C4–7)cycloalkane, indene, cyclopenta(C4–7)cycloalkane,

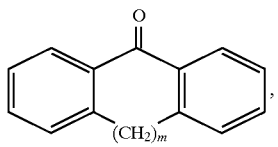

in which m is 0 or 1, or benzene fused 4–7 membered heterocyclic ring consisting of one nitrogen, one sulfur or one oxygen atom;

$R^1$ is hydrogen or C1–4 alkyl;

$R^2$ is hydrogen or C1–4 alkyl;

n is 1–3;

$R^3$ each, independently, is (1) hydrogen, C1–6 alkyl, C1–6 alkoxy, halogen, nitro, methylthio, trifluoromethyl or cyano, (2) —Q—T—U—$R^5$ in which Q is bond or C1–6 alkylene;

T is bond, —O—,

—S—, —SO$_2$—, —NR$^7$— or —NR$^7$CO—, in which $R^7$ is hydrogen, C1–4 alkyl, phenyl or phenyl(C1–4)alkyl and nitrogen atom in —NR$^7$CO— may be connected with —Q— or —U—; U is bond, C1–6 alkylene, C2–6 alkenylene, C2–6 alkynylene or C1–6 alkylene —O—, in which oxygen atom can be connected with $R^5$ only;

$R^5$ is (i) C4–7 cycloalkyl, (ii) phenyl, (iii) diphenylmethyl or (iv) 4–7 membered heterocyclic ring consisting of one nitrogen, one sulfur or one oxygen, or the benzene fused 4–7 membered heterocyclic ring consisting of one nitrogen, one sulfur or one oxygen, or rings in (i), (ii), (iii), (iv) of $R^5$ may be substituted by 1–3 of C1–10 alkyl, C1–10 alkoxy, hydroxy, halogen, trifluoromethyl, nitro or COR$^6$, in which $R^6$ is C1–4 alkyl, NR$^8$R$^9$, in which $R^8$ and $R^9$ each, independently, is hydrogen or C1–4 alkyl;

or —Q—T—U—$R^5$ is C7–10 alkyl, C7–10 alkoxy;

or non-toxic salts thereof, with the proviso that, the compounds wherein (i) T is —O—, or —NR$^7$—, and U is bond and $R^5$ is diphenylmethyl in —Q—T—U—$R^5$ represented by $R^3$, when Ⓩ is thiophene, E is bond and Ⓓ is benzene or naphthalene, (ii) T is —O—, or —NR$^7$—, and U is C1–6 alkylene and $R^5$ is phenyl or diphenylmethyl in —Q—T—U—$R^5$ represented by $R^3$, when Ⓩ is thiophene, E is bond and Ⓓ is benzene or naphthalene, (iii) Ⓩ is pyrrole included nitrogen substituted by $R^4$, in which $R^4$ is hydrogen, C1–3 alkyl or phenyl, A is bond or methylene, E is bond Ⓓ is benzene, $R^2$ is hydrogen or methyl and $R^3$ each, independently, is hydrogen or halogen, are excluded;

with a pharmaceutical carrier or coating.

2. A method for the treatment of diseases induced by the excess generation of dihydrotestosterone in mammals, alopecia, acnes, hypertrophy of prostate and prostatic cancer, which comprises the administration of an effective amount of a compound of the formula (Ia) depicted in claim 1 or non-toxic salts thereof.

3. A compound of the formula (1b):

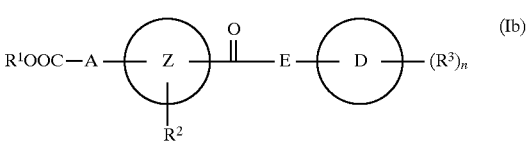 (Ib)

wherein

Ⓩ is pyrrole included nitrogen substituted by $R^4$, thiophene, furan, imidazole included nitrogen substituted by $R^4$, thiazole, oxazole, triazole included nitrogen substituted by $R^4$, in which R⁴ is hydrogen, C1–4 alkyl, phenyl or phenyl(C1–4)alkyl;
A is bond, C1–6 alkylene or C2–6 alkenylene;
E is bond or C1–6 alkylene;
Ⓓ is benzene, C4–7 cycloalkane, naphthalene, benzo(C4–7)cycloalkane, indene, cyclopenta(C4–7)cycloalkane,

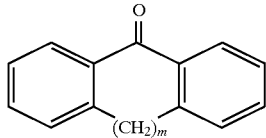

in which m is 0 or 1, or benzene fused 4–7 membered heterocylic ring consisting of one nitrogen, one sulfur or one oxygen atom;
R is hydrogen or C1–4 alkyl,
R² is hydrogen or C1–4 alkyl;
n is 1–3
R³ each, independently, is (1) hydrogen, C1–6 alkyl, C1–6 alkoxy, halogen, nitro, methylthio, trifluoromethyl or cyano,
(2) —Q—T—U—R⁵ in which Q is bond or C1–6 alkylene;
T is bond, —O—,

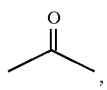

—S—, —S₂, —NR⁷— or —NR⁷CO—, in which R⁷ is hydrogen, C1–4 alkyl, phenyl or phenyl(C1–4)alkyl and nitrogen atom in —NR⁷CO— may be connected with —Q— or —U—;
U is bond, C1–6 alkylene, C2–6 alkenylene, C2–6 alkynylene or C1–6 alkylene —O—, in which oxygen atom can be connected with R⁵ only;
R⁵ is (i) C4–7 cycloalkyl, (ii) phenyl, (iii) diphenylmethyl or (iv) 4–7 membered heterocyclic ring consisting of one nitrogen, one sulfur or one oxygen,
or the benzene fused 4–7 membered heterocyclic ring consisting of one nitrogen, one sulfur or one oxygen, or rings in (i), (ii), (iii), (iv) of R⁵ may be substituted by 1–3 of C1–10 alkyl, C1–10 alkoxy, hydroxy, halogen, trifluoromethyl, nitro or COR⁶, in which R⁶ is C1–4 alkyl, NR⁸R⁹, in which R⁸ and R⁹ each, independently, is hydrogen or C1–4 alkyl;
or —Q—T—U—R⁵ is C7–10 alkyl, C7–10 alkoxy;
or non-toxic salts thereof,
with the proviso that,
(a) compounds wherein
(i) T is —O—, or —NR⁷—, and U is bond and R⁵ is diphenylmethyl in —Q—T—U—R⁵ represented by R³, when Ⓩ is thiophene, E is bond and Ⓓ is benzene or naphthalene,
(ii) T is —O—, or —NR⁷—, and U is C1–6 alkylene and R⁵ is phenyl or diphenylmethyl in —Q—T—U—R⁵ represented by R³, when Ⓩ is thiophene, E is bond and Ⓓ is benzene or naphthalene, are excluded;
(b) at least one R³ of (R³)ₙ is a substituent selected from group (2) that is —Q—T—U—R⁵, when E is bond and Ⓓ is benzene;

(c) all R³ of (R³)ₙ are not hydrogen at the same time, when E is bond and Ⓓ is C4–7 cycloalkane, or E is methylene and Ⓓ is benzene;
(d) 2-[5-[2-chloro-4-(1H-pyrrol-1-yl)benzoyl]thiophen-2-yl]acetic acid and methyl ester thereof and 2-[5-[2-chloro-4-(2,5-dimethyl-1H-pyrrol-1-yl)benzoyl]thiophen-2-yl]acetic acid and methyl ester thereof are excluded;
(e) when Ⓩ is pyrrole included nitrogen substituted by R₄, pyrrole is substituted on 2 position by

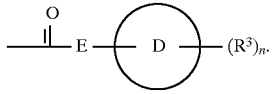

4. A compound according to claim 3, where in Ⓩ is pyrrole included nitrogen substituted by R⁴, in which R⁴ is the same meaning as defined in claim 3.
5. A compound according to claim 3, where in Ⓩ is thiophene.
6. A compound according to claim 3, where in Ⓩ is furan.
7. A compound according to claim 3, where in Ⓩ is imidazole included nitrogen substituted by R⁴, in which R⁴ is the same meaning as defined in claim 3.
8. A compound according to claim 3, where in Ⓩ is thiazole.
9. A compound according to claim 3, where in Ⓩ is oxazole.
10. A compound according to claim 3, where in Ⓩ is triazole included nitrogen substituted by R⁴, in which R⁴ is the same meaning as defined in claim 3.
11. A compound according to claim 3, where in Ⓓ is benzene.
12. A compound according to claim 3, where in Ⓓ is C4–7 cycloalkane.
13. A compound according to claim 3, where in Ⓓ is naphthalene, benzo(C4–7)cycloalkane, indene, cyclopenta(C4–7)cycloalkane or

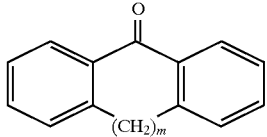

in which m is 0 or 1.
14. A compound according to claim 3, wherein Ⓓ is benzene fused 4–7 membered heterocyclic ring containing one nitrogen, one sulfur or one oxygen atom.
15. A compound according to claim 3, which is selected from the group consisting of
2-[5-(4-t-Butylcyclohexaylcarbonyl)-1-methylpyrrol-2-yl]acetic acid,
2-[5-(4-Phenylcyclohexylcarbonyl)-1-methylpyrrol-2-yl]acetic acid, and
2-[5-[3-(1,2,3,4-Tetrahydro-2-naphthyl)propylcarbonyl]-1-methylpyrrol-2-yl]acetic acid.
16. A compound according to claim 3, which is
2-[5-(4-Phenylbenzoyl)-2-thienyl]acetic acid, or
2-[5-(4-Phenoxybenzoyl)-2-thienyl]acetic acid.
17. A compound according to claim 3, which is
2-[5-(4-Phenylbenzoyl)-2-furanyl]acetic acid.
18. A compound according to claim 3, which is
2-[2-(4-Phenylbenzoyl)-1-methylimidazol-5-yl]acetic acid, or
2-(4-Phenylbenzoyl)-1-methylimidazol-5-yl carboxylic acid.

19. A compound according to claim 3, which is selected from the group consisting of
2-[5-[4-(4-Ethylphenyl)benzoyl]-1-methylpyrrol-2-yl] acetic acid,
2-[5-(4-Cyclohexylbenzoyl)-1-methylpyrrol-2-yl]acetic acid,
2-[5-(4-Phenylbenzoyl)-1-methylpyrrol-2-yl]acetic acid,
2-[5-(4-Benzylbenzoyl)-1-methylpyrrol-2-yl]acetic acid,
2-[5-(3-Benzoylbenzoyl)-1-methylpyrrol-2-yl]acetic acid,
2-[5-(4-Benzoylbenzoyl)-1-methylpyrrol-2-yl]acetic acid,
2-[5-(3-Phenoxybenzoyl)-1-methylpyrrol-2-yl]acetic acid,
2-[5-(4-Phenoxybenzoyl)-1-methylpyrrol-2-yl]acetic acid,
2-[5-(4-Benzyloxybenzoyl)-1-methylpyrrol-2-yl]acetic acid,
2-[5-[4-(4-Ethylbenzyloxy)benzoyl]-1-methylpyrrol-2-yl] acetic acid,
2-[5-[4-(4-Isopropylbenzyloxy)benzoyl]-1-methylpyrrol-2-yl]acetic acid,
2-[5-[4-(4-Butylbenzyloxy)benzoyl]-1-methylpyrrol-2-yl] acetic acid,
2-[5-[4-(4-t-Butylbenzyloxy)benzoyl]-1-methylpyrrol-2-yl] acetic acid,
2-[5-(4-Phenylbenzyl)carbonyl-1-methylpyrrol-2-yl]acetic acid,
2-[5-(3-Benzyloxy-4-methoxybenzoyl)-1-methylpyrrol-2-yl]acetic acid,
2-[5-(4-Benzyloxy-2-methylbenzoyl)-1-methylpyrrol-2-yl] acetic acid,
2-[5-(4-Benzyloxy-2,3-dimethylbenzoyl)-1-methylpyrrol-2-yl]acetic acid,
2-[5-(3-Phenylpropyl)carbonyl-1-methylpyrrol-2-yl]acetic acid,
2-[5-(4-Phenylbutyl)carbonyl-1-methylpyrrol-2-yl]acetic acid,
2-[5-(4-Heptylphenyl)benzoyl-1-methylpyrrol-2-yl]acetic acid,
3-[5-(4-Phenylbenzoyl)-1-methylpyrrol-2-yl]-2-propenoic acid,
3-[5-(4-Phenylbenzoyl)-1-methylpyrrol-2-yl]propionic acid,
4-[5-(4-Phenylbenzoyl)-1-methylpyrrol-2-yl]butanoic acid,
2-[5-(4-Phenylbenzoyl)-1-benzylpyrrol-2-yl]acetic acid,
5-[5-(4-Phenylbenzoyl)-1-methylpyrrol-2-yl]pentanoic acid,
4-[5-[4-(4-isopropylbenzyloxy)benzoyl]-1-methylpyrrol-2-yl]butanoic acid,
5-[5-[4-(4-isopropylbenzyloxy)benzoyl]-1-methylpyrrol-2-yl]pentanoic acid,
2-[5-(2-Phenoxybenzoyl)-1-methylpyrrol-2-yl]acetic acid,
2-[5-(4-Cyclohexyloxybenzoyl)-1-methylpyrrol-2-yl]acetic acid,
2-[5-[4-(4-Nitrophenyloxy)benzoyl]-1-methylpyrrol-2-yl] acetic acid,
2-[5-(3-Diphenylmethylaminobenzoyl)-1-methylpyrrol-2-yl]acetic acid,
2-[5-(3-Dibenzylaminobenzoyl)-1-methylpyrrol-2-yl]acetic acid,
2-[5-(4-Dibenzylaminomethylbenzoyl)-1-methylpyrrol-2-yl]acetic acid,
2-[5-(3-Phenylcarbonylaminobenzoyl)-1-methylpyrrol-2-yl]acetic acid,
2-[5-(4-Phenylcarbonylaminobenzoyl)-1-methylpyrrol-2-yl]acetic acid,
2-[5-(4-Phenylthiomethylbenzoyl)-1-methylpyrrol-2-yl] acetic acid,
2-[5-(3-Phenylthiomethylbenzoyl)-1-methylpyrrol-2-yl] acetic acid,
2-[5-(4-Phenylsulfonylmethylbenzoyl)-1-methylpyrrol-2-yl]acetic acid,
2-[5-(3-Phenylsulfonylmethylbenzoyl)-1-methylpyrrol-2-yl]acetic acid,
2-[5-[4-(2-Phenylethyl)benzoyl]-1-methylpyrrol-2-yl]acetic acid,
2-[5-[4-(2-Phenylethynyl)benzoyl]-1-methylpyrrol-2-yl] acetic acid,
2-[5-[4-(2-Phenyletheneyl)benzoyl]-1-methylpyrrol-2-yl] acetic acid,
2-[5-(5-Phenylpentylcarbonyl)-1-methylpyrrol-2-yl]acetic acid,
2-[5-[3-(Pyrrol-1-yl)benzoyl]-1-methylpyrrol-2-yl]acetic acid,
2-[5-[4-(Pyrrol-1-yl)benzoyl]-1-methylpyrrol-2-yl]acetic acid,
2-[5-[4-(Isoindol-2-yl)benzoyl]-1-methylpyrrol-2-yl]acetic acid,
2-[5-[4-(2,5-Dimethylpyrrol-1-yl)benzoyl]-1-methylpyrrol-2-yl]acetic acid,
2-[5-[3-(2-Thienyl)benzoyl]-1-methylpyrrol-2-yl]acetic acid,
2-[5-[4-(2-Thienyl)benzoyl]-1-methylpyrrol-2-yl]acetic acid,
2-[5-[4-(5-Bromo-2-thienyl)benzoyl]-1-methylpyrrol-2-yl] acetic acid,
2-[5-(4-Heptylbenzoyl)-1-methylpyrrol-2-yl]acetic acid,
2-[5-[4-(4-Propylcyclohexyl)benzoyl]-1-methylpyrrol-2-yl] acetic acid,
2-[5-[4-(4-Methylphenyl)benzoyl]-1-methylpyrrol-2-yl] acetic acid,
2-[5-[4-(2-Methylphenyl)benzoyl]-1-methylpyrrol-2-yl] acetic acid,
2-[5-[4-(4-Propylphenyl)benzoyl]-1-methylpyrrol-2-yl] acetic acid,
2-[5-[4-(4-Methoxyphenyl)benzoyl]-1-methylpyrrol-2-yl] acetic acid,
2-[5-[4-(4-Fluorophenyl)benzoyl]-1-methylpyrrol-2-yl] acetic acid,
2-[5-[4-(4-Chlorophenyl)benzoyl]-1-methylpyrrol-2-yl] acetic acid,
2-[5-[4-(3-Chloro-4-fluorophenyl)benzoyl]-1-methylpyrrol-2-yl]acetic acid,
2-[5-[4-(3-Trifluoromethylphenyl)benzoyl]-1-methylpyrrol-2-yl]acetic acid,
2-[5-[4-(4-Trifluoromethylphenyl)benzoyl]-1-methylpyrrol-2-yl]acetic acid,
2-[5-[4-(3-Nitrophenyl)benzoyl]-1-methylpyrrol-2-yl]acetic acid,
2-[5-[4-(4-Methylcarbonylphenyl)benzoyl]-1-methylpyrrol-2-yl]acetic acid,
2-[5-[4-(4-Dimethylaminocarbonylphenyl)benzoyl]-1-methylpyrrol-2-yl]acetic acid,
5-(4-Phenylbenzoyl)-1-methylpyrrol-2-yl carboxylic acid,
5-(4-Phenylbenzoyl)-1H-pyrrol-2-yl carboxylic acid,
2-[5-[4-(4-Bromophenyl)benzoyl]-1-methylpyrrol-2-yl] acetic acid,
2-[5-(4-Phenylbenzoyl)-1H-pyrrol-2-yl]acetic acid,
2-[5-[4-(2,4-Dichlorophenyl)benzoyl]-1-methylpyrrol-2-yl] acetic acid,
2-[5-[4-(3,5-Dichlorophenyl)benzoyl]-1-methylpyrrol-2-yl] acetic acid,
2-[5-(3-Methyl-4-phenylbenzoyl)-1-methylpyrrol-2-yl] acetic acid,
2-[5-[4-[(N-methyl-N-phenyl)carbamoyl]benzoyl]-1-methylpyrrol-2-yl]acetic acid,
2-[5-[4-(N-phenylcarbamoyl)benzoyl]-1-methylpyrrol-2-yl] acetic acid, 2-[5-[4-[N-(diphenylmethyl)carbamoyl]benzoyl]-1-methylpyrrol-2-yl]acetic acid, 2-[5-[4-[(N-methyl-N-benzyl)carbamoyl]benzoyl]-1-methylpyrrol-2-yl]acetic acid, 2-[5-[4-(N-benzylcarbamoyl)benzoyl]-1-methylpyrrol-2-yl]acetic acid, 2-[5-[4-(2-phenoxyethoxy)benzoyl]-1-methylpyrrol-2-yl]acetic acid, and 2-[5-(3-phenylpropanoyl)-1-methylpyrrol-2-yl]acetic acid.

20. A compound according to claim 3, which is 2-[5-(2-Naphthyl)carbonyl-1-methylpyrrol-2-yl]acetic acid, or 2-[5-(9-Oxofluoren-2-yl)carbonyl-1-methylpyrrol-2-yl]acetic acid.

21. A compound according to claim 3, which is 2-[5-(2-benzothienyl)carbonyl-1-methylpyrrol-2-yl]acetic acid, or 2-[5-(2-benzofuranyl)carbonyl-1-methylpyrrol-2-yl]acetic acid.

22. A pharmaceutical composition according to claim 1, which is selected from the group consisting of 2-[5-(4-Methylbenzoyl)-1-methylpyrrol-2-yl]acetic acid, 2-[5-(4-t-Butylbenzoyl)-1-methylpyrrol-2-yl]acetic acid, 2-[5-(3,5-Di-t-butylbenzoyl)-1-methylpyrrol-2-yl]acetic acid, 2-[5-(4-Hexyloxybenzoyl)-1-methylpyrrol-2-yl]acetic acid, 2-[5-(4-Trifluoromethylbenzoyl)-1-methylpyrrol-2-yl]acetic acid, 2-[5-(4-Isobutylbenzoyl)-1-methylpyrrol-2-yl]acetic acid, 2-[5-(4-Nitrobenzoyl)-1-methylpyrrol-2-yl]acetic acid, 2-[5-(4-isopropyloxybenzoyl)-1-methylpyrrol-2-yl]acetic acid, and 2-[5-benzylcarbonyl-1-methylpyrrol-2-yl]acetic acid.

23. A compound which is 2-[5-(4-Iodobenzoyl)-1-methylpyrrol-2-yl]acetic acid.

24. A compound which is selected from the group consisting of 2-[4-(4-Phenylbenzoyl)-1-methylpyrrol-2-yl]acetic acid, 4-(4-Phenylbenzoyl)-1-methylpyrrol-2-yl carboxylic acid, and 4-(4-Phenylbenzoyl)-1H-pyrrol-2-yl carboxylic acid.

* * * * *